US011603360B2

(12) United States Patent
Janka

(10) Patent No.: US 11,603,360 B2
(45) Date of Patent: *Mar. 14, 2023

(54) METHOD FOR PRODUCING PURIFIED DIALKYL-FURAN-2,5-DICARBOXYLATE

(71) Applicant: Eastman Chemical Company, Kingsport, TN (US)

(72) Inventor: Mesfin Ejerssa Janka, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 333 days.

This patent is subject to a terminal disclaimer.

(21) Appl. No.: 16/914,618

(22) Filed: Jun. 29, 2020

(65) Prior Publication Data

US 2020/0331879 A1  Oct. 22, 2020

Related U.S. Application Data

(63) Continuation of application No. 15/875,352, filed on Jan. 19, 2018, now Pat. No. 10,696,645.

(60) Provisional application No. 62/534,897, filed on Jul. 20, 2017.

(51) Int. Cl.
| | |
|---|---|
| *C07D 307/68* | (2006.01) |
| *C07D 307/42* | (2006.01) |
| *B01D 3/06* | (2006.01) |
| *C07B 63/00* | (2006.01) |
| *C07B 33/00* | (2006.01) |
| *C07B 63/02* | (2006.01) |
| *B01D 3/14* | (2006.01) |
| *B01D 3/00* | (2006.01) |

(52) U.S. Cl.
CPC ............ *C07D 307/68* (2013.01); *B01D 3/002* (2013.01); *B01D 3/06* (2013.01); *B01D 3/065* (2013.01); *B01D 3/143* (2013.01); *C07B 33/00* (2013.01); *C07B 63/00* (2013.01); *C07B 63/02* (2013.01); *C07D 307/42* (2013.01)

(58) Field of Classification Search
CPC .................................................... C07D 307/68
See application file for complete search history.

(56) References Cited

U.S. PATENT DOCUMENTS

| | | | |
|---|---|---|---|
| 2,551,731 A | 5/1951 | Drewitt | |
| 3,225,066 A | 12/1965 | Lew | |
| 3,845,100 A | 10/1974 | Kusak | |
| 3,852,247 A | 12/1974 | Vizurraga | |
| 4,405,736 A | 9/1983 | Kubota et al. | |
| 4,876,327 A | 10/1989 | Vriesema et al. | |
| 4,977,283 A | 12/1990 | Leupold et al. | |
| 5,958,581 A | 9/1999 | Khanarian et al. | |
| 5,959,066 A | 9/1999 | Charbonneau et al. | |
| 6,025,061 A | 2/2000 | Khanarian et al. | |
| 6,063,464 A | 5/2000 | Charbonneau et al. | |
| 6,063,465 A | 5/2000 | Charbonneau et al. | |
| 6,063,495 A | 5/2000 | Charbonneau et al. | |
| 6,103,825 A | 8/2000 | Frischinger et al. | |
| 6,107,447 A | 8/2000 | Kreuder et al. | |
| 6,126,992 A | 10/2000 | Khanarian et al. | |
| 6,140,422 A | 10/2000 | Khanarian et al. | |
| 6,342,300 B1 | 1/2002 | Bengs et al. | |
| 6,359,070 B1 | 3/2002 | Khanarian et al. | |
| 6,737,481 B1 | 5/2004 | Kurian et al. | |
| 6,914,120 B2 | 7/2005 | Germroth et al. | |
| 7,052,764 B2 | 5/2006 | Chang et al. | |
| 7,385,081 B1 | 6/2008 | Gong | |
| 7,638,592 B2 | 12/2009 | Benecke et al. | |
| 7,700,788 B2 | 4/2010 | Lilga et al. | |
| 8,143,355 B2 | 3/2012 | Matsuda et al. | |
| 8,658,810 B2 | 2/2014 | Shaikh et al. | |
| 8,859,788 B2 | 10/2014 | Partin et al. | |
| 8,912,349 B2 | 12/2014 | Shaikh et al. | |
| 8,916,349 B2 | 12/2014 | Nadeau et al. | |
| 9,029,581 B2 | 5/2015 | Partin et al. | |
| 9,169,229 B2 | 10/2015 | Parker et al. | |
| 9,376,414 B2 | 6/2016 | Van Haveren et al. | |
| 10,696,645 B2 | 6/2020 | Janka | |
| 2003/0055271 A1 | 3/2003 | Grushin et al. | |

(Continued)

FOREIGN PATENT DOCUMENTS

| | | |
|---|---|---|
| CA | 2235270 A1 | 4/1997 |
| EP | 0741134 A1 | 11/1996 |

(Continued)

OTHER PUBLICATIONS

Obrecht. Helvetica Chimica Acta, 1997, 80, 531-537. (Year: 1997).*
Gandini Alessandro, et al., "The Furan Counterpart of Poly(ethylene terephthalate): An Alternative Material Based on Renewable Resources", Journal of Polymer Science: Part A: Polymer Chemistry, vol. 47, (2009), pp. 295-298.
Partenheimer, Walt, et al., "Synthesis of 2,5-Diformylfuran and Furan-2,5-Dicarboxylic Acid by Catalytic Air-Oxidation of 5-Hydroxymethylfurfural. Unexpectedly Selective Aerobic Oxidation of Benzyl Alcohol to Benzaldehyde with Metal/Bromide Catalysts", *Adv. Synth. Catal.* 2001, 343, pp. 102-111.
Akutin et al., N.N. USSR Patent 162962, 1964; Chem. Abstr. 1964, 61, p. 8441e.

(Continued)

*Primary Examiner* — Noble E Jarrell
(74) *Attorney, Agent, or Firm* — Steven A. Owen

(57) ABSTRACT

Disclosed is a purified dialkyl furan dicarboxylate (DAFD) vapor composition containing at least 99.5 wt. % DAFD; 5-(alkoxycarbonyl) furan-2-carboxylic acid (ACFC) that, if present, is present in an amount of not more than 1000 ppm, alkyl-5-formylfuran-2-carboxylate (AFFC) that, if present, is present in an amount of not more than 1000 ppm, 5-(dialkoxymethyl)furan-2-carboxylic acid (DAFCA) that if present, is present in an amount of not more than 1000 ppm, and alkyl 5-(dialkoxymethyl)furan-2-carboxylate (ADAFC) that if present, is present in an amount of not more than 1000 ppm, in each case based on the weight of the DAFD vapor composition.

5 Claims, 3 Drawing Sheets

(56) References Cited

U.S. PATENT DOCUMENTS

| | | | |
|---|---|---|---|
| 2006/0205977 | A1 | 9/2006 | Sumner et al. |
| 2008/0081883 | A1 | 4/2008 | King, II et al. |
| 2008/0182944 | A1 | 7/2008 | Benecke et al. |
| 2009/0018264 | A1 | 1/2009 | Fuseya |
| 2009/0124763 | A1 | 5/2009 | Matsuda et al. |
| 2009/0124829 | A1 | 5/2009 | Gong |
| 2009/0143602 | A1 | 6/2009 | Benecke et al. |
| 2009/0156841 | A1 | 6/2009 | Sanborn et al. |
| 2010/0081774 | A1 | 4/2010 | Benecke et al. |
| 2010/0174044 | A1 | 7/2010 | Eritate |
| 2010/0210867 | A1 | 8/2010 | Bustamante et al. |
| 2010/0331568 | A1 | 12/2010 | Brandvold |
| 2012/0123085 | A1 | 5/2012 | Grushin et al. |
| 2013/0345557 | A1 | 12/2013 | Kim et al. |
| 2014/0024754 | A1 | 1/2014 | Becker et al. |

FOREIGN PATENT DOCUMENTS

| | | | |
|---|---|---|---|
| FR | 2 723 946 | A1 | 3/1996 |
| JP | 2008291243 | A | 12/2008 |
| JP | 2008291244 | A | 12/2008 |
| JP | 2008308578 | A | 12/2008 |
| JP | 2009215467 | A | 9/2009 |
| JP | 2009-242312 | A | 10/2009 |
| JP | 2009-263509 | A | 11/2009 |
| WO | WO 2009/118377 | A1 | 10/2009 |
| WO | WO 2009/135921 | A1 | 11/2009 |
| WO | WO 2010/077133 | A1 | 7/2010 |
| WO | WO 2010/132740 | A2 | 11/2010 |
| WO | WO 2010/140599 | A1 | 12/2010 |
| WO | WO 2010/151346 | A1 | 12/2010 |
| WO | WO 2011/023590 | A1 | 3/2011 |
| WO | WO 2011-043660 | A2 | 4/2011 |
| WO | WO 2011-043661 | A1 | 4/2011 |
| WO | WO 2012-101015 | A1 | 8/2012 |
| WO | WO 2013184661 | A1 | 12/2013 |

OTHER PUBLICATIONS

Lewkowski, J., "Synthesis, Chemistry and Applications of 5-Hydroxymethylfurfural and its Derivatives." ARKIVOC, 2001, pp. 17-54.
Lewkowski, J., "Convenient Synthesis of Furan-2,5-dicarboxylic Acid and Its Derivatives", Polish J. Chem, 75, pp. 1943-1946, (2001).
Haworth, W. N., et al.; "The Conversion of Sucrose into Furan Compound. Part II. Some 2: 5-Disubstituted Tetrahydrofurans and their Products of Ring Scission"; Journal of The Chemical Society, No. 1, (1945), pp. 1-4.
Gonis, George, et al.; "The Preparation of Furan-2,5-dicarboxylic acid", J. Org. Chem., vol. 27, No. 8 (1962). pp. 2946-2947.
Lukes, et al., CS Patent 87340 (1959); Chem. Abstr. 1961, 55, p. 17084.
Manasek et al., 1963, 6, 35; Chem. Abstr. 1964, 60, p. 8180a.
Rodivilowa et al., Khim. Tekhnol. 11 1968, 7, 818; Chem. Abstr. 1969, 70, p. 4685v.
Copending U.S. Appl. No. 13/530,789, filed Jun. 22, 2012, Lee Reynolds Partin, et al.
Copending U.S. Appl. No. 13/530,738, filed Jun. 22, 2012, Ashfaq Shaikh, et al.
Copending U.S. Appl. No. 13/530,765, filed Jun. 22, 2012, Ashfaq Shaikh, et al.
Notification of Transmittal of the International Search Report and the Written Opinion of the International Search Authority, or the Declaration—International Application No. PCT/US2013/044919 dated Aug. 22, 2013.
USPTO Office Action for Co-pending U.S. Appl. No. 13/530,738 dated Jul. 26, 2013.
Notification of Transmittal of the International Search Report and the Written Opinion of the International Search Authority, or the Declaration—International Application No. PCT/US2013/044922 dated Sep. 23, 2013.
Sanderson, R D, et al.; "Synthesis and Evaluation of Dialkyl Furan-2, 5-Dicarboxylates as Plasticizers for PVC", Journal of Applied Polymer Science, vol. 53, No. 13, (1994), pp. 1785-1793.
Yoder P A, et al; "Ueber Dehydroshleimsaure: eine neue Darstellungsmethode, sowie verschiedene Salze und Ester derselben", Berichte Der Deutschen Chemischen Gesellschaft Abteilung B: Abhandlungen, vol. 34, No. 3, (1901), pp. 3446-3462.
USPTO Office Action for Co-Pending U.S. Appl. No. 13/530,789 dated Oct. 31, 2013.
USPTO Office Action for Co-Pending U.S. Appl. No. 13/530,765 dated Oct. 31, 2013.
Notification of Transmittal of the International Search Report and the Written Opinion of the International Search Authority, or the Declaration—International Application No. PCT/US2013/044927 dated Oct. 18, 2013.
USPTO Notice of Allowance for Co-pending U.S. Appl. No. 13/530,738 dated Jan. 22, 2014.
USPTO Office Action for Co-Pending U.S. Appl. No. 13/530,789 dated Apr. 2, 2014.
USPTO Office Action for Co-Pending U.S. Appl. No. 13/530,765 dated Apr. 11, 2014.
Copending U.S. Appl. No. 15/875,257, filed Jan. 18, 2018, Mesfin Ejerssa Janka.
Copending U.S. Appl. No. 15/875,352, filed Jan. 18, 2018, Mesfin Ejerssa Janka.
March, Jerry, "Advanced organic chemistry: 1-15 reactions, mechanisms, and structure", $4^{th}$ edition, John Wiley & Sons, Inc, 1992, pp. 392-393.
USPTO Office Action for Co-Pending U.S. Appl. No. 15/875,257 dated Oct. 25, 2017.
Wang, Cong et al.; Cytotoxic Compounds From the Deep-Sea Sediment-Derived Streptomyces Malaysiensis OUCMDZ-2167; Chinese Jounal of Organic Chemistry, 2016, pp. 658-666.
USPTO Office Action for Co-pending U.S. Appl. No. 15/875,352 dated Jan. 28, 2019.
Dikusar, E.A., et al.; "Synthesis of 2-R-1,3-Dioxanes, Derivatives of Functionally Substituted Aldehydes of Vanillin Series"; Russian Journal of Organic Chemistry, vol. 49(2), 2013; pp. 221-227.
Sirbu, D., et al.; Synthesis and properties of a meso-tris-ferrocene appended zing(II) porphyrin and a critical evaluation of its dye sensitized solar cell (DSSC) performance; RSC Adv., 2014, 4, 22733-22742.
USPTO Office Action for Co-Pending U.S. Appl. No. 15/875,257 dated Mar. 28, 2019.
USPTO Office Action for CO-Pending U.S. Appl. No. 15/875,352 dated Oct. 4, 2019.
Konig, B., et al.; "Science of Synthesis"; 2001, 9, pp. 183-285.
Notice of Allowance received in U.S. Appl. No. 15/875,257 dated Apr. 8, 2020.
Copending U.S. Appl. No. 16/914,618, filed Jun. 29, 2020, Mesfin Ejerssa Janka.

* cited by examiner

METHOD FOR PRODUCING PURIFIED DIALKYL-FURAN-2,5-DICARBOXYLATE

1. CROSS-REFERENCE TO RELATED APPLICATION

This application is a continuation of application Ser. No. 15/875,352 filed on Jan. 19, 2018, which claims the benefit of Provisional Application No. 62/534,897, filed Jul. 20, 2017, the disclosure of which is incorporated herein by reference in its entirety.

2. FIELD OF THE INVENTION

The invention relates to the processes for the production of purified dialkyl-furan-2,5-dicarboxylate (DAFD) vapor and purified DAFD compositions made therefrom.

3. BACKGROUND OF THE INVENTION

Aromatic dicarboxylic acids such as terephthalic acid and isophthalic acid or their di-esters, dimethyl terephthalate as for example, are used to produce a variety of polyester products, important examples of which are poly (ethylene terephthalate) and its copolymers. The aromatic dicarboxylic acids are synthesized by the catalytic oxidation of the corresponding dialkyl aromatic compounds which are obtained from fossil fuels such as those disclosed in US 2006/0205977 A1. Esterification of these diacids using excess alcohol produces the corresponding di-esters has been disclosed in US2010/0210867A1. There is a growing interest in the use of renewable resources as feed stocks for the chemical industries mainly due to the progressive reduction of fossil reserves and their related environmental impacts.

Furan-2,5-dicarboxylic acid ("FDCA") is a versatile intermediate considered as a promising closest biobased alternative to terephthalic acid and isophthalic acid. Like aromatic diacids, FDCA can be condensed with diols such as ethylene glycol to make polyester resins similar to polyethylene terephthalate (PET) as disclosed in Gandini, A.; Silvestre, A. J; Neto, C. P.; Sousa, A. F.; Gomes, M. *J. Poly. Sci. A* 2009, 47, 295. FDCA has been prepared by oxidation of 5-(hydroxymethyl) furfural (5-HMF) under air using homogenous catalysts as disclosed in US2003/0055271 A1 and in Partenheimer, W.; Grushin, V. V. *Adv. Synth. Catal.* 2001, 343, 102-111. However, achieving high yields has proved difficult. A maximum of 44.8% yield using Co/Mn/Br catalysts system and a maximum of 60.9% yield was reported using Co/Mn/Br/Zr catalysts combination.

The crude FDCA obtained by the oxidation processes must to be purified before they are suitable for end-use applications. JP patent application, JP209-242312A, disclosed crude FDCA purification process using sodium hydroxide/sodium hypochlorite and/or hydrogen peroxide followed by acid treatment of the disodium salt to obtain pure FDCA. This multi-step purification process generates wasteful by-products.

Therefore, there is a need for an inexpensive and high yield process for the purification of crude FDCA that minimizes the creation of additional waste products and lends itself to efficient separation step(s).

4. SUMMARY OF THE INVENTION

There is now provided a process for the manufacture of DAFD vapor comprising:
a. feeding a furan-2,5-dicarboxylic acid ("FDCA") composition to an esterification reaction zone; and
b. in the presence of an alcohol compound, conducting an esterification reaction in the esterification reaction zone to react FDCA with said alcohol compound to form a crude diester composition comprising dialkyl furan-2,5-dicarboxylate ("DAFD"), the alcohol compound, 5-(alkoxycarbonyl)furan-2-carboxylic acid (ACFC), alkyl furan-2-carboxylate (AFC), alkyl-5-formylfuran-2-carboxylate (AFFC), 5-(dialkoxymethyl)furan-2-carboxylic acid (DAFCA) and alkyl 5-(dialkoxymethyl) furan-2-carboxylate (ADAFC), and
c. separating at least a portion of the alcohol compound from the crude diester composition in a flash zone using a physical separation process to produce:
  (i) a vapor alcohol composition, comprising said alcohol compound, taken as an overhead stream that is rich in the concentration of alcohol, relative to the alcohol concentration in the crude diester composition feeding the flash zone, and
  (ii) a first liquid DAFD rich composition, comprising DAFD, ACFC, AFC, AFFC, DAFCA, and ADAFC that is rich in the total concentration of DAFD relative to the total concentration of DAFD in the crude diester composition feeding the flash zone; and
d. separating at least a portion of DAFD from the first liquid DAFD rich composition in a product recovery zone;
wherein the process produces a composition comprising:
  (i) at least 99.5 wt. % DAFD;
  (ii) 5-(alkoxycarbonyl)furan-2-carboxylic acid (ACFC) that if present, is present in an amount of not more than 1000 ppm,
  (iii) alkyl-5-formylfuran-2-carboxylate (AFFC) that if present, is present in an amount of not more than 1000 ppm
  (iv) 5-(dialkoxymethyl)furan-2-carboxylic acid (DAFCA) that if present, is present in an amount of not more than 1000 ppm, and
  (v) alkyl 5-(dialkoxymethyl)furan-2-carboxylate (ADAFC) that if present, is present in an amount of not more than 1000 ppm,
in each case based on the weight of the DAFD vapor composition.

There is also provided a purified dialkyl furan dicarboxylate (DAFD) vapor composition comprising:
  (i) at least 99.5 wt. % DAFD;
  (ii) 5-(alkoxycarbonyl)furan-2-carboxylic acid (ACFC) that if present, is present in an amount of not more than 1000 ppm,
  (iii) alkyl-5-formylfuran-2-carboxylate (AFFC) that if present, is present in an amount of not more than 1000 ppm
  (iv) 5-(dialkoxymethyl)furan-2-carboxylic acid (DAFCA) that if present, is present in an amount of not more than 1000 ppm, and
  (v) alkyl 5-(dialkoxymethyl)furan-2-carboxylate (ADAFC) that if present, is present in an amount of not more than 1000 ppm,
in each case based on the weight of the DAFD vapor composition.

There is also provided a purified liquid DAFD composition comprising:

(i) at least 99.9 wt. % DAFD;
(ii) not more than 100 ppm ACFC,
(iii) not more than 100 ppm AFFC,
(iv) not more than 10 ppm furan dicarboxylic acid (FDCA),
(v) not more than 100 ppm DAFCA, and
(vi) not more than 100 ppm ADAFC,
in each case based on the weight of the DAFD vapor composition.

There is also provided a solids DAFD composition comprising solid particles of DAFD, wherein said solids comprise:
(i) at least 99.5 wt. % liquid DAFD;
(ii) 5-(alkoxycarbonyl)furan-2-carboxylic acid (ACFC) that if present, is present in an amount of not more than 1000 ppm,
(iii) alkyl-5-formylfuran-2-carboxylate (AFFC) that if present, is present in an amount of not more than 1000 ppm,
(iv) 5-(dialkoxymethyl)furan-2-carboxylic acid (DAFCA) that if present, is present in an amount of not more than 1000 ppm,
(v) alkyl 5-(dialkoxymethyl)furan-2-carboxylate (ADAFC) that if present, is present in an amount of not more than 1000 ppm,
(vi) not more than 1 wt. % water, and
(vii) not more than 1 wt. % solids,
in each case based on the weight of the purified liquid DAFD composition.

5. BRIEF DESCRIPTION OF THE DRAWINGS

6. DETAILED DESCRIPTION OF THE INVENTION

Figure 1:
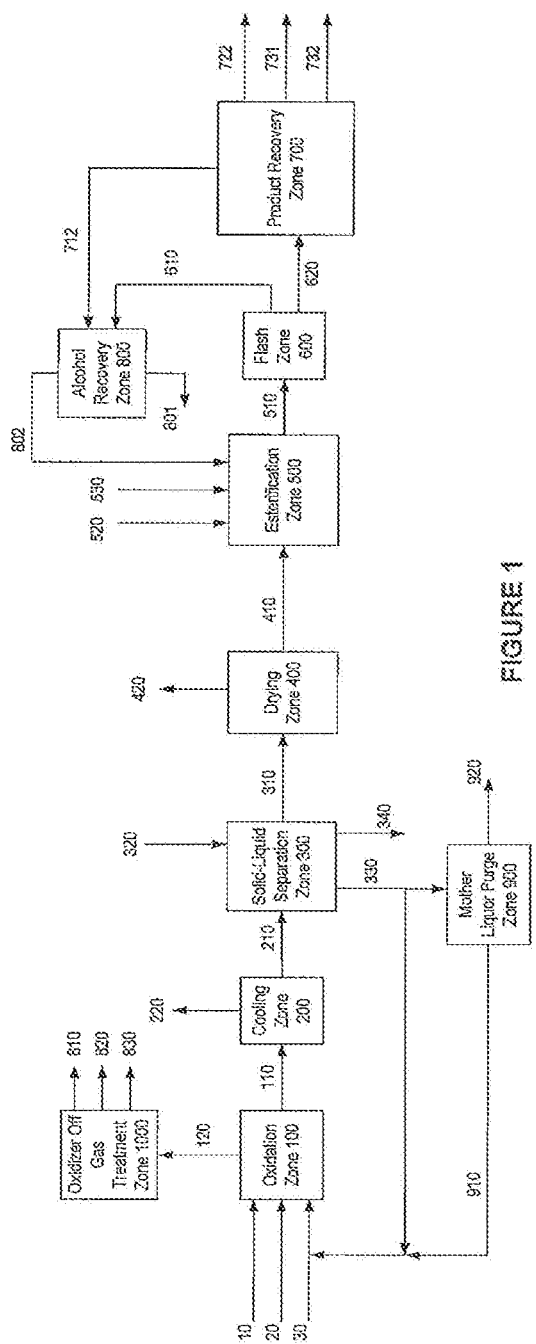
FIG. 1 is a flow diagram of the process for making both FDCA and purified DAFD.

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "containing," "having," "has," and "have" have the same open-ended meaning as "comprising," "comprises," and "comprise" provided above.

As used herein, the terms "including," "includes," and "include" have the same open-ended meaning as "comprising," "comprises," and "comprise" provided above.

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds).

The present description uses specific numerical values to quantify certain parameters relating to the invention, where the specific numerical values are not expressly part of a numerical range. It should be understood that each specific numerical value provided herein is to be construed as providing literal support for a broad, intermediate, and narrow range. The broad range associated with each specific numerical value is the numerical value plus and minus 60 percent of the numerical value, rounded to two significant digits. The intermediate range associated with each specific numerical value is the numerical value plus and minus 30 percent of the numerical value, rounded to two significant digits. The narrow range associated with each specific numerical value is the numerical value plus and minus 15 percent of the numerical value, rounded to two significant digits. For example, if the specification describes a specific temperature of 62° F., such a description provides literal support for a broad numerical range of 25° F. to 99° F. (62° F.+/−37° F.), an intermediate numerical range of 43° F. to 81° F. (62° F.+/−19° F.), and a narrow numerical range of 53° F. to 71° F. (62° F.+/−9° F.). These broad, intermediate, and narrow numerical ranges should be applied not only to the specific values, but should also be applied to differences between these specific values. Thus, if the specification describes a first pressure of 110 psia and a second pressure of 48 psia (a difference of 62 psia), the broad, intermediate, and narrow ranges for the pressure difference between these two streams would be 25 psia to 99 psia, 43 psia to 81 psia, and 53 psia to 71 psia, respectively.

The word "rich" in reference to a composition means the concentration of the referenced ingredient in the composition is higher than the concentration of the same ingredient in the feed composition to the separation zone by weight. For example, a liquid DAFD rich composition means that the concentration of DAFD in the liquid DAFD rich composition is greater than the concentration of DAFD in the stream feeding the separation zone, in this case, the crude diester composition.

All amounts are by weight unless otherwise specified. All references to ppm are on a mass basis.

As illustrated in FIG. 1, a dicarboxylic acid composition stream 410, which can be either dried carboxylic acid solids or a wet cake containing carboxylic acid, in each case the carboxylic acid comprising furan dicarboxylic acid ("FDCA"), and an alcohol composition stream 520 are fed to the esterification reaction zone 500. The solid dicarboxylic acid composition 410 can be shipped via truck, ship, or rail as solids to a plant or facility for the manufacture of the diester composition. The process for the oxidation of the oxidizable material containing the furan group can be integrated with the process for the manufacture of the diester composition. An integrated process includes co-locating the two manufacturing facilities, one for oxidation and the other for esterification, within 10 miles, or within 5 miles, or within 2 miles, or within 1 mile, or within ½ mile of each other. An integrated process also includes having the two manufacturing facilities in solid or fluid communication with each other. If a solid dicarboxylic acid composition is produced, the solids can be conveyed by any suitable means, such as air or belt, to the esterification facility. If a wet cake dicarboxylic acid composition is produced, the wet cake can be moved by belt or pumped as a liquid slurry to the facility for esterification.

The esterification zone 500 comprises at least one esterification reactor. The dicarboxylic acid composition comprising FDCA is fed to the esterification zone and, in the presence of an alcohol compound, an esterification reaction is conducted in the esterification reaction zone to react FDCA with said alcohol compound to form a crude diester composition comprising dialkyl furan-2,5-dicarboxylate ("DAFD"), the alcohol compound, 5-(alkoxycarbonyl) furan-2-carboxylic acid (ACFC), alkyl furan-2-carboxylate (AFC), and alkyl-5-formylfuran-2-carboxylate (AFFC). The crude diester composition may optionally contain a catalyst if a homogeneous esterification catalyst is used.

The alcohol composition comprises one or more types of alcohol compounds. Examples include compounds represented by the structure R—OH wherein R can range from 1 to 6 carbons, or 1 to 5 carbon atoms, or 1 to 4 carbon atoms, or 1 to 3 carbon atoms, or 1 to 2 carbon atoms, preferably methanol. R can be branched or unbranched, saturated or unsaturated, and cyclic or acyclic. Desirably, R is an unbranched, saturated, acyclic alkyl group. The alcohol composition contains at least 50 wt. %, or at least 60 wt %, or at least 70 wt %, or at least 80 wt. %, or at least 90 wt. %, or at least 95 wt %, or at least 97 wt %, or at least 98 wt. %, or at least 99 wt. % alcohol compounds based on the weight of the alcohol composition. Desirably, the alcohol composition comprises methanol.

The crude diester composition produced in the esterification zone 500 is the reaction product of at least FDCA with the alcohol composition to produce DAFD, where the alkyl moiety is an alkyl group containing 1 to 6 carbon atoms, and at least a portion of the alkyl moiety corresponds to the alcohol residue. In the case of a reaction between FDCA and methanol, the diester reaction product comprises dimethyl furan-2,5-dicarboxylate ("DMFD"). The esterification reaction of FDCA with methanol to produce DMFD comprises multiple reaction mechanisms as illustrated below. One reaction mechanism comprises reacting one mole of FDCA with one mole of Methanol to produce a mole of 5-(methoxycarbonyl)furan-2-carboxylic acid (MCFC) and water. One mole of MCFC can then react with one mole of methanol to produce one mole of the desired product DMFD and water. Because both DMFD and MCFC are present in an esterification reaction zone, the crude diester composition will also contain MCFC in addition to the unreacted hydroxyl compounds and DMFD. A commercial process to produce purified DMFD must allow for the separation of DMFD and MCFC downstream of the esterification zone.

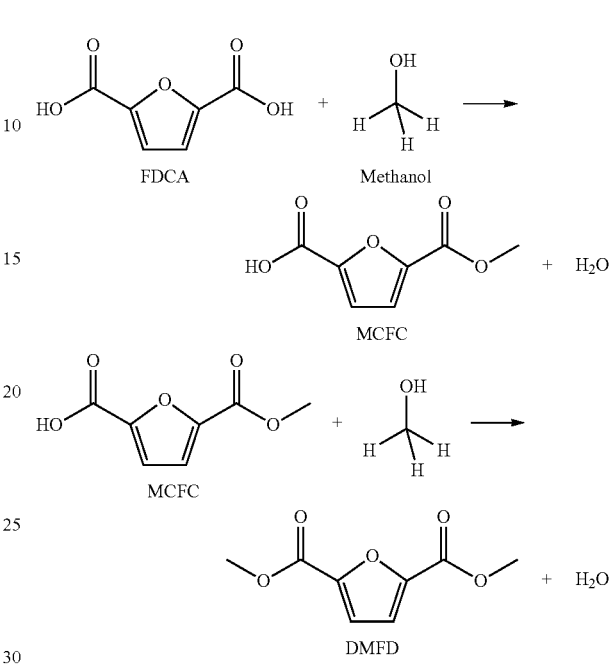

Esterification by-products are also formed in reaction zone 500 and comprise chemicals with boiling points both higher and lower than DMFD. Esterification by-products formed in the esterification reaction zone comprise methyl acetate, alkyl furan-2-carboxylate (AFC), alkyl 5-formyl-furan-2-carboxylate (AFFC), and 5-(alkoxycarbonyl)furan-2-carboxylic acid (ACFC). Many other by-products are possible depending upon the impurities contained within the FDCA feedstock. One of the major by products in the crude FDCA that can form impurities during esterification is FFCA. FFCA can react with the alcohol to form 5-(dialkoxymethyl)furan-2-carboxylic acid (DAFCA) and alkyl 5-(dialkoxymethyl)furan-2-carboxylate (ADAFC) impurities:

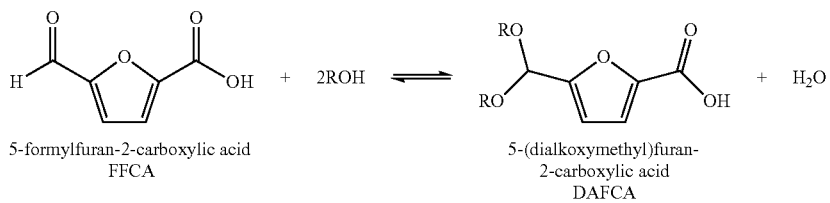

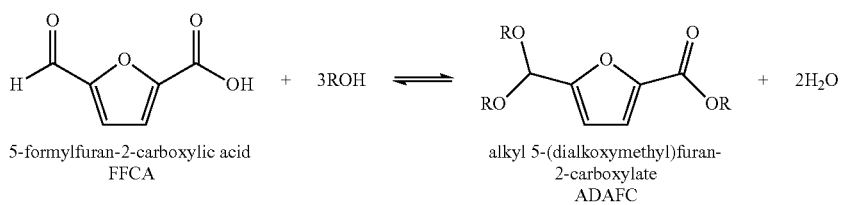

When methanol is used as an esterification alcohol, its reaction with FFCA impurity in the crude FDCA can generate 5-(dimethoxymethyl)furan-2-carboxylic acid (DMFCA) and methyl 5-(dimethoxymethyl)furan-2-carboxylate (MDMFC):

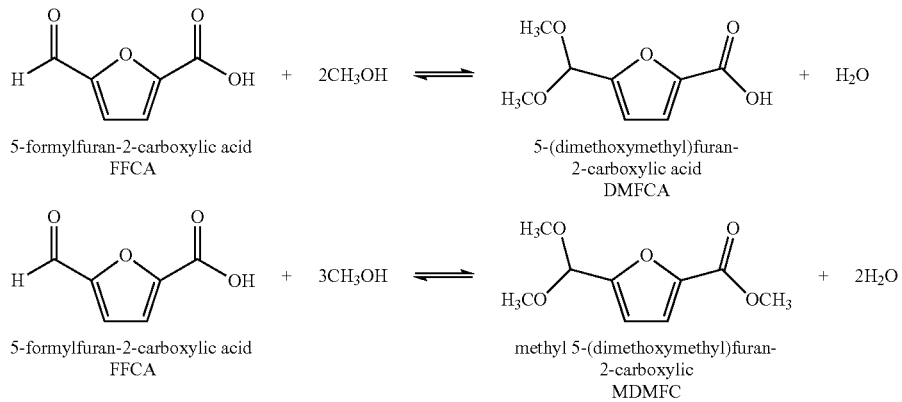

5-formylfuran-2-carboxylic acid
FFCA 5-(dimethoxymethyl)furan-2-carboxylic acid
DMFCA 5-formylfuran-2-carboxylic acid
FFCA methyl 5-(dimethoxymethyl)furan-2-carboxylic
MDMFC A commercial process to produce a purified DAFD stream must allow for the separation of impurities from the crude di-ester composition exiting as stream 510. Further, at least a portion of these impurities can be purged from the process wherein purging involves isolation of the impurities and routing them from the process.

Figure 2:
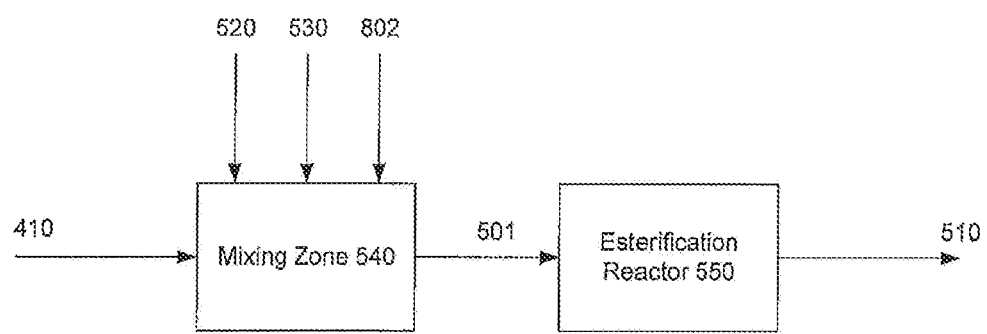
FIG. 2 is a flow diagram illustrating a feed of raw materials to a mixing zone prior to feeding the slurry to an esterification reactor.

It is desirable to first mix the FDCA composition with the alcohol prior to conducting an esterification reaction under esterification conditions. As illustrated in FIG. 2, there is provided a mixing zone 540 and esterification reactor 550 within the esterification zone 500. The dicarboxylic acid composition 410 comprising FDCA, an alcohol composition 520, optionally an esterification catalyst system 530, and optionally an alcohol recycle stream 802 comprising a recycled alcohol at least one of which is the same type of compounds as fed in stream 520 are mixed in the mixing zone 540 to generate mixed reactor feed stream 501. In one embodiment, streams 520 and 802 comprise methanol.

Mixing in zone 540 may be accomplished by any equipment known in the art for mixing liquid and solids, such as continuous in line static mixers, batch agitated vessels, and or continuous agitated vessels, and the like. The theoretical amount of alcohol required for the reaction with each mole of FDCA in the esterification zone, or the esterification reactor 550, or in the mixing zone 540, is two moles. The total amount of alcohol present in mixing zone 540 is desirably in excess of the theoretical amount required for the esterification reaction.

For example, the molar ratio of alcohol to FDCA moles ranges from greater than 2:1, or at least 2.2:1, or at least 2.5:1, or at least 3:1, or at least 4:1, or at least 8:1, or at least 10:1, or at least 15:1, or at least 20:1, or at least 25:1, or at least 30:1 and can go as high as 40:1. Suitable molar ratios are within a range of alcohol to FDCA from 10:1 to 30:1.

To the mixing zone 540 may also be fed an esterification catalyst system as stream 530 if a catalyst is used. The catalyst is can be heterogeneous or desirably a homogenous catalyst under esterification reaction conditions, and can also be homogeneous in the mixing zone. Known organometallic esterification catalysts can be used such as the acetate or other carboxylate or glycolate of cobalt, copper and manganese, cadmium, lead, lithium, and zinc in amounts conventionally used for esterifying terephathalic acid. Other organic catalysts can be employed such as sulfuric acid, tosylic acid, and Lewis acids.

The mixed reactor feed stream 501 is routed to esterification reactor 550 to generate a crude diester composition discharged from the esterification reactor 550 as liquid crude diester stream 510. The crude diester composition 510 discharged from the esterification zone 500 desirably contains DAFD present in an amount of at least 5 wt %, or at least 8 wt. %, or at least 10 wt. %, or at least 15 wt. %, or at least 20 wt. %, and up to 40 wt. %, or up to 35 wt. %, based on the weight of the whole crude diester composition, and desirably in each case based on the weight of the liquid phase. At the high temperatures, high pressure, and/or high alcohol concentration under esterification conditions, the DAFD present in the crude diester composition is solubilized and the solids concentration is generally not more than 5 wt. %, or not more than 2 wt. %, or not more than 1 wt. %, or not more than 0.5 wt. %, or not more than 0.1 wt. %, although the amount of solids can be higher as the concentration of unreacted alcohol is diminished and the reaction temperature is reduced. If solids are present, at least 95 wt. %, or at least 96 wt. %, or at least 97 wt. %, or at least 98 wt. %, or at least 99 wt. % of the solids are unreacted FDCA solids.

The yield of DAFD in the crude diester composition desirably high. Suitable yields are at least 55 mole %, or at least 60 mole %, or at least 65%, or at least 70 mole %, or at least 75 mole %, or at least 80 mole %, or at least 85 mole %, or at least 90 mole %, or at least 95 mole %, or at least 99 mole %. The yield of DAFD in the crude diester stream is calculated as follows:

(mol of DAFD in the crude diester composition in the liquid phase/starting mol of FDCA)*100%.

The crude FDCA slurry stream can be fed into the esterification reactor at a rate corresponding to a desired throughput in a continuous process for the production of a purified DAFD vapor composition. Examples of suitable rates for the production of a purified DAFD vapor composition stream include an average of at least 1000 kg/day, or at least 10,000 kg/day, or at least 20,000 kg/day, or at least 50,000 kg/day, or at least 75,000 kg/day, or at least 100,000 kg/day, or at least 200,000 kg/day of a purified DAFD vapor composition, on a 24 hour basis over the course of any three months.

Esterification may be accomplished in batch or continuous reactors and comprises one or multiple reaction vessels that are capable of providing acceptable reaction residence time, temperature, and pressure. The esterification reaction residence time ranges from 0.5 hr to about 10 hours. The esterification temperature ranges from 150° C. to below the supercritical temperature of the alcohol selected to ensure that the alcohol stays in liquid phase at reaction pressures. Suitable reaction temperatures can range from 150° C. to 250° C., or 150° C. to 240° C., or from 200° C. to 230° C. Particularly suitable is an upper range of 240° C. in the case methanol is used as the alcohol. The esterification pressure within the esterification reactor is sufficient to maintain the alcohol compound in the liquid phase and will vary with the temperature selected. Suitable pressure ranges are from about 250 psig to about 2000 psig, or from 400 psig to 1500 about psig.

The crude diester composition is taken from the esterification reactor in the esterification zone 500 in a stream 510 and fed to a flash zone 600 as shown in FIG. 1. At least a portion of alcohol compound in the crude diester composition is separated from the crude diester stream in the flash zone 600 in a physical separation process to produce a first liquid DAFD rich composition stream 620 containing liquid DAFD, and in which the concentration of DAFD in the DAFD rich composition is higher than the concentration of DAFD in the crude diester composition feeding the flash zone 600. In the flash zone, the crude diester composition experiences a pressure letdown to flash alcohol resulting also in evaporative cooling.

The crude diester composition exits the esterification zone 500 at elevated temperatures, typically at a temperature of at least 150° C., or at least 170° C., or at least 180° C., or at least 190° C., or at least 200° C., or at least 210° C., or at least 220° C., or at least 230° C., or at least 240° C., and in each case below the supercritical temperature of the alcohol. To take advantage of the sensible heat energy already present in crude diester composition, one may simply conduct the physical separation under a pressure that is lower relative to the pressure over the crude diester stream upon entry into the separation zone, and thereby take off alcohol through reduced pressure to produce a first liquid DAFD rich composition as stream 620. This can be accomplished without applying heat energy to the separation vessel for separation purposes to thereby reduce energy consumption (e.g. adiabatic flash).

The flash zone 600 can comprise one or more vessels for flash separation through pressure reduction operated in series or parallel without application of external heat energy to effect the separation. For example, the flash zone 600 can comprise one or more evaporative flash unit operations, or can comprise one or more distillation columns. The alcohol separation zone can comprise both a flash evaporation unit and a distillation column. The separation zone may be operated in a batch or continuous mode.

Desirably, the flash zone 600 contains at least a flash evaporation unit such as a flash tank. One may conduct staged flash evaporation in multiple vessels. The pressure in the flash unit operation can range from 0 psig to about 150 psig, or from 0 psig to about 50 psig, or from 0 psig to 35 psig. If alcohol is separated under a reduced pressure relative to the pressure of the crude diester composition at the entry to the physical separation vessel, it is desirable that the pressure within the flash vessel is below the vapor pressure of the alcohol at the temperature of the crude diester stream at the entry port to the flash vessel.

The temperature of the first liquid DAFD rich composition stream 620 discharged from the flash zone 600 is not particularly limited. It will be lower than the temperature of the crude diester stream entering the flash zone due to evaporative cooling. In one embodiment, the temperature of the first liquid DAFD rich composition stream 620 is at least 5° C. cooler, or at least 20° C. cooler, or at least 50° C. cooler, or at least 75° C. cooler, or at least 100° C. cooler, or at least 120° C. cooler than the crude diester composition temperature entering the flash zone 600. One may employ a series of flash vessels that have small incremental temperature drops such that the cumulative temperature drop of all the vessels within the zone add up to at least these stated values.

A vapor alcohol composition stream 610 is generated in the flash zone 600. The vapor alcohol composition stream 610 comprises alcohol, some water, and optionally a small (e.g. less than 0.1 wt %) DAFD can also be present. The vapor alcohol composition stream 610 is rich in the concentration of alcohol, relative to the alcohol concentration in the crude diester composition 510. Desirably, the concentration of alcohol in the vapor alcohol composition 610 comprises at least 70 wt. % alcohol, or at least 80 wt. % alcohol, or at least 90 wt. %, or at least 95 wt. % alcohol.

The vapor alcohol composition stream 610 is fed to an alcohol recovery zone 800. The alcohol recovery zone generates a purified alcohol stream 802 comprising alcohol that is depleted in the concentration of water alcohol relative to the concentration of water in the vapor alcohol composition stream 610, and generates a water stream 801 that is rich in the concentration of water relative to the concentration of water in the vapor alcohol stream 610.

The alcohol recovery zone 800 can comprise one or more distillation columns to effect the separation of alcohol from water. The distillation column can be dedicated to receive a feed of the vapor alcohol composition 610 or the vapor alcohol composition 610 can be first condensed and fed to the distillation column. The purified alcohol composition 802 may be one or more vapor distillates and if desired, at least a portion can be condensed and at least a portion can be fed as a recycle stream back to the esterification zone 500.

Alternatively, the vapor alcohol composition gaseous overhead stream 610, or liquid if condensed, can be fed to a shared distillation column in alcohol recovery zone 800 that also receives a feed of a second alcohol rich stream 712. It is desired to use a shared distillation apparatus to reduce capital costs.

The first liquid DAFD rich composition stream 620 comprises DAFD rich (a higher concentration) in the concentration of DAFD relative to the concentration of DAFD present in the crude diester stream 510 exiting the esterification zone 500. The concentration of DAFD in the DAFD rich stream can be increased by at or at least 20%, or at least 30%, or at least 40%, or at least 50%, or at least 70%, or at least 90%, or at least 100%, or at least 150%, or at least 200%, or at least 250%, or at least 300%, or at least 400%, or at least 500%, over the concentration of DAFD in the crude diester composition 510. The DAFD rich stream desirably contains DAFD present in an amount of at least 5 wt. %, or at least 10 wt %, or at least 20 wt %, or at least 30 wt %, or at least 40 wt %, or at least 50 wt %, or at least 60 wt %, and in each case up to 70 wt. %, or up to 80 wt %, in each case based on the weight of the DAFD rich composition.

The first liquid DAFD rich stream desirably contains no solids. If present, the solids comprise DAFD and/or unreacted FDCA or other by-products reacting with DAFD and/or FDCA. The solids concentration in the DAFD composition may contain no more than 55 wt. %, or up to 45 wt. %, or up to 35 wt. %, or up to 28 wt. %, or up to 15 wt. %, or up to 10 wt. %, or up to 5 wt. %, or up to 3 wt. %, or up to 2 wt. %, and if present, an amount of greater than zero, each based on the weight of the first liquid DAFD rich composition 620.

The first liquid DAFD rich composition stream 620 also contains any alcohol that did not separate in the flash zone 600, some water, and a quantity of some or all of the by-products mentioned above. The amount of alcohol in the first liquid DAFD rich stream is greater than zero, or at least 1 wt. %, or at least 2 wt. %, or at least 3 wt. %, or at least 5 wt. %, or at least 10 wt. %, or at least 15 wt. %, and up to 60 wt. %, or up to 50 wt. %, or up to 40 wt. %, based on the weight of the DAFD rich stream.

As shown in FIG. 1, the first liquid DAFD rich composition stream 620 is fed to a product recovery zone 700 to separate at least a portion of DAFD from the first liquid DAFD rich composition in the product recovery zone using one or more physical separation processes to produce:

(i) a purified DAFD vapor composition rich in the concentration of DAFD relative to the concentration of DAFD in the first liquid DAFD rich composition; and (ii) a liquid ACFC composition that is rich in the concentration of ACFC relative to the concentration of ACFC in the first liquid DAFD rich composition; and (iii) a vapor AFC composition comprising AFC that is rich in the concentration of AFC relative to the concentration of AFC in the first liquid DAFD rich composition; and (iv) a second vapor alcohol composition, comprising alcohol, that is rich in the concentration of alcohol, relative to the first liquid DAFD rich composition.

The product recovery zone 700 may contain one or more distillation columns to effect one or more separations.

Figure 3:
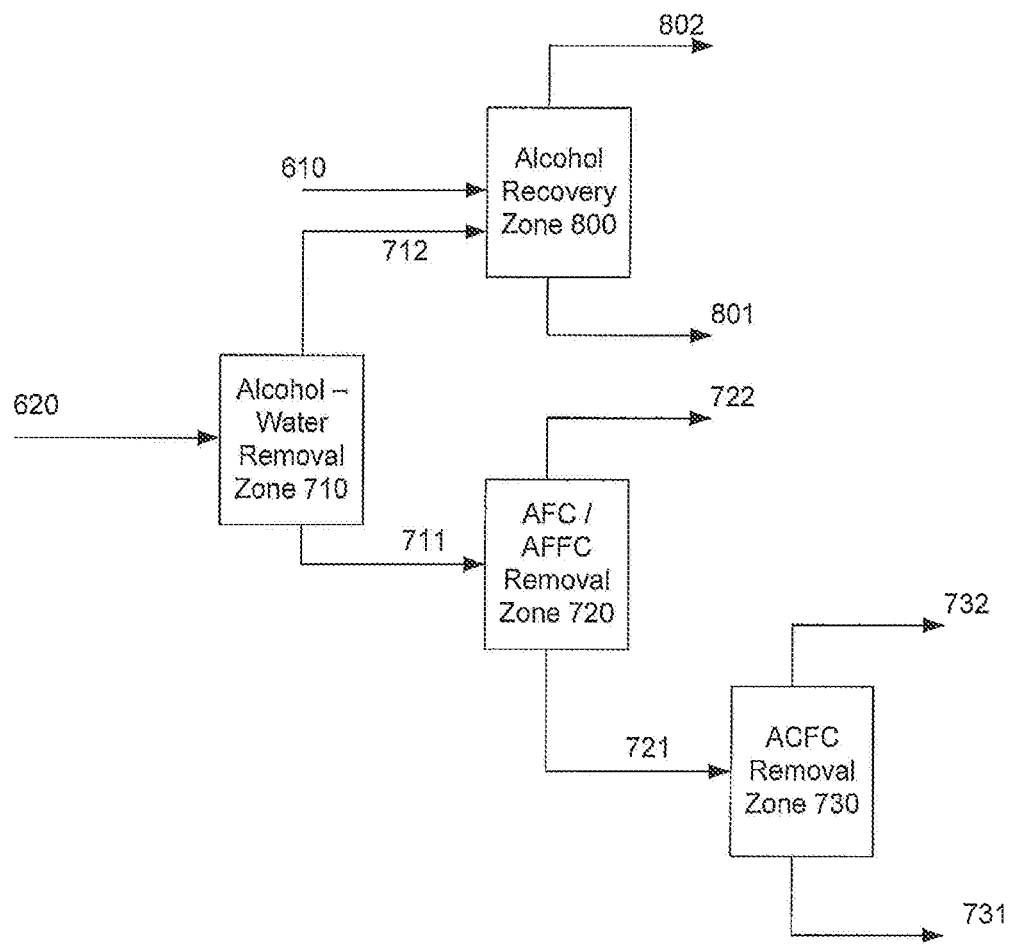
FIG. 3 is a flow diagram depicting the process of producing a purified DAFD vapor composition using a combination of separation zones.

As an example, the product recovery zone 700 may contain an alcohol-water removal zone 710, as shown in FIG. 3, comprising a physical separation unit to separate alcohol from the first liquid DAFD rich composition, thereby producing a second alcohol composition stream 712 discharged from the top of the column that is rich in the concentration of alcohol relative to the concentration of alcohol in the first liquid DAFD rich composition stream 620, and a second liquid DAFD rich composition stream 711 comprising DAFD that is rich in the concentration of DAFD relative to the concentration of DAFD in the first liquid DAFD rich composition stream 620. Desirably the concentration of alcohol in the second liquid DAFD rich composition is depleted (or lower) relative to the concentration of alcohol in the first liquid DAFD rich composition. Also, desirably the concentration of DAFD in the second alcohol composition stream 712 discharged from the top of the column is depleted relative to the concentration of DAFD in the second liquid DAFD rich composition stream 711.

An example of a suitable devices for carrying out the separation of alcohol from the first liquid DAFD rich composition stream 620 is any type of distillation column (tray or packed).

The second alcohol composition stream 712 can, if desired, be fed directly to the alcohol recovery zone 800 as a vapor to separate water from the second alcohol composition stream 712. Alternatively, the second alcohol composition stream 712 can, if desired, be condensed, with a portion of the condensed alcohol composition fed back to the column as reflux and a portion of the condensed alcohol composition fed to the alcohol recovery zone 800 as a liquid. Thus, stream 712 fed to the alcohol recovery zone 800 is either a liquid and/or a vapor. The alcohol recovery zone 800 separates alcohol from the second alcohol composition stream 712. The alcohol recovery zone 800 can also be used to accept a feed of the first vapor alcohol composition stream 610 to separate alcohol from the first vapor alcohol composition stream 610, and the same distillation column can be used to accept feeds 610 and 712. Alternatively, a second distillation column can be used to accept feed 610.

Throughout this description, it is to be understood that any vapor stream generated in the process, such as in each distillation apparatus, can be condensed, and the condensation can occur inside the column, outside the column, such as after the vapor is discharged from the rectification section of the distillation apparatus, and it can be partially or fully condensed. Alternatively, the vapor stream does not have to be condensed at all. It is also to be understood that any values describing the concentration of an ingredient in a vapor stream can be measured on a liquid stream condensed from the vapor stream in question if the condensables in the vapor stream are fully condensed.

Alcohol recovery zone 800 generates a purified alcohol composition stream 802 that is suitable for use as a recycle stream fed to the esterification zone 500 if desired, and a water rich stream 801 that is enriched in the concentration of water relative to the concentration of water in the purified alcohol composition stream 802. The concentration of water in the water rich stream 801 is desirably at least 98 wt. %, or at least 99 wt. %, or at least 99.5 wt. %.

Examples of suitable devices to separate alcohol from water in the alcohol recovery zone include a distillation column, with trays, or packed or both.

The vaporous purified alcohol composition stream 802, whether or not condensed to use as a recycle stream to the esterification zone, contains less than 10 wt. % water, or less than 5 wt. % water, or less than 1 wt. % water, or less than 0.5 wt. % water, and less than 0.001 wt. % DAFD, or less than 0.0001 wt. % DAFD, each based on the weight of the purified alcohol composition stream 802. In one embodiment, the purified alcohol recycle stream 802 comprises methanol at a purity of greater than 99.0 wt. % based on the weight of the purified alcohol composition stream.

The second liquid DAFD rich composition stream 711 discharged from the alcohol water removal zone 710 contains DAFD at a concentration of at least 80 wt. %, or at least 85 wt. %, or at least 90 wt. %, or at least 92 wt. %, and up to 99 wt. %, or up to 98 wt. %, or up to 97 wt. %, or up to 96 wt. %, each based on the weight of the second liquid DAFD rich composition stream 711. The amount of alcohol in the second liquid DAFD rich composition stream is desirably less than 1 wt. %, or less than 0.1 wt. %, or less than 0.01 wt. %, or less than 0.001 wt. %. The amount of water in the second liquid DAFD rich composition 711 is desirably less than 1 wt. %, or less than 0.5 wt. %, or less than 0.2 wt. %. The concentration of DAFD in the second liquid DAFD rich composition 711 can be higher than the concentration of DAFD in the first liquid DAFD rich composition stream 620 by at least 10 wt %, or at least 20 wt %, or at least 30 wt %, or at least 40 wt %. The cumulative concentration of water and alcohol in the second liquid DAFD rich composition 711 is depleted relative to the concentration of water an alcohol in the first liquid DAFD rich composition 620 by a factor of at least 100×, or at least 300×, or at least 500×, or at least 700×.

The second liquid DAFD rich composition stream 711 contains not only DAFD, but also ACFC, AFC, and AFFC. As shown in FIG. 3, the second liquid DAFD rich composition 711 is fed to an AFC/AFFC removal zone 720 to separate at least a portion of AFC from the liquid DAFD rich composition using a physical separation process to produce an AFC rich vapor composition 722 rich in the concentration of AFC relative to the concentration of AFC in the second liquid DAFD rich composition 711, and a partially purified liquid DAFD rich composition stream 721 comprising DAFD and ACFC that is rich in the concentration of DAFD relative to the concentration of DAFD in the second liquid DAFD rich composition 711. Since AFC rich vapor composition 722 is rich in the concentration of AFC relative to the concentration of AFC in the second liquid DAFD rich composition 711, it is necessarily also rich in the concentration of AFC relative to the concentration of AFC in the first liquid DAFD rich composition stream 620. Since DAFD in the partially purified liquid DAFD rich composition stream 721 is rich in the concentration of DAFD relative to the concentration of DAFD in the second liquid DAFD rich composition 711, it is necessarily also rich in the concentration of DAFD relative to the concentration of DAFD in the first liquid DAFD rich composition stream 620.

An example of a suitable physical separation method is to distill the second liquid DAFD rich composition 711. Suitable distillation pot temperatures range in zone 720 from 200° C. to less than the boiling point of DAFD under the operating conditions. Suitable temperatures range from 210° C. to 280° C., or 220° C. to 260° C., or 230° C. to 250° C. The second liquid DAFD rich composition is desirably distilled at a vacuum to avoid degrading the DAFD product in the second DAFD rich composition in the pot that might otherwise occur at higher temperatures. The second DAFD rich composition can be distilled at pressures ranging from 1 psia to atmospheric pressure. The column desirably has 10 to 70 trays, 10 to 60 trays to, 10 to 50 trays, where a tray can be a valve tray, sieve tray, bubble cap tray, or an equivalent height of a packed bed. The distillation operating temperature desirably is set create an AFC vapor composition and desirably to take off AFC vapor as a distillate, which can optionally be partially or fully condensed and a portion returned to the column as reflux. In another embodiment, the distillation conditions can be set to also take off AFFC in addition to AFC as a vapor overhead such that the concentration of AFFC in the AFC rich vapor composition 722 is enriched in the concentration of AFFC relative to the concentration of AFFC in the second liquid DAFD rich stream 711. In this embodiment, since AFC rich vapor composition 722 is rich in the concentration of AFFC relative to the concentration of AFFC in the second liquid DAFD rich composition 711, it is necessarily also rich in the concentration of AFFC relative to the concentration of AFFC in the first liquid DAFD rich composition stream 620.

The reflux ratio to achieve desired purities will vary with the number of trays and the mass of distillate produced.

The composition of the AFC rich vapor stream 722 contains AFC. The AFC rich vapor stream composition comprises at least 5 wt. % AFC, or at least 10 wt. % AFC, or at least 15 wt. % AFC, or at least 20 wt. % AFC, or at least 25 wt. % AFC. The AFC rich vapor stream composition optionally comprises at least 2 wt. % AFFC, or at least 5 wt. % AFFC, or at least 10 wt. % AFFC, or at least 20 wt. % AFFC, or at least 30 wt. % AFFC, or at least 40 wt. % AFFC, or at least 50 wt. % AFFC, or at least 60 wt. % AFFC. The concentration of AFFC in the AFC rich vapor stream 722 can be higher than the concentration of AFC, in some cases by a factor of 1.5×, or 2×, or 2.5×. The concentration of DAFD in the AFC rich vapor composition 722 is depleted relative to the concentration of DAFD in the second liquid DAFD rich composition stream 711. The concentration of DAFD in the AFC rich vapor composition 722 can be less than 10 wt. % DAFD, or less than 5 wt. % DAFD, or less than 4 wt. % DAFD, or less than 3 wt. % DAFD, or less than 2 wt. % DAFD, or less than 1 wt. % DAFD, each based on the weight of the AFC rich vapor composition. The concentration of AFC and AFFC in the AFC rich vapor composition stream 722 can be at least 20 wt %, or at least 40 wt. %, or at least 60 wt. %, or at least 80 wt. %, or at least 90 wt. %, or at least 95 wt. %, each based on the weight of all ingredients in the AFC rich vapor composition 722.

The concentration of AFC in the AFC rich vapor composition stream 722 is desirably increased by a factor of at least 5×, or at least 10×, or at least 15× and up to 80×, or up to 70×, or up to 50×, on a weight basis, relative to the concentration of AFC in the second liquid DAFD rich composition 711.

The composition of the partially purified liquid DAFD rich stream 721 contains DAFD and ACFC. The concentration of each of these ingredients based on the weight of the partially purified liquid DAFD rich stream 721 is as follows:

DAFD: at least 90 wt. %, or at least 92 wt. %, or at least 95 wt. %, or at least 97 wt. %, or at least 98 wt. %, and up to 99.9 wt. %, or up to 99.5 wt. %, or up to 99.0 wt. %, or up to 98.5 wt. %, or up to 98 wt. %; and ACFC: at least 0.05 wt. %, or at least 0.1 wt. %, or at least 0.5 wt. %, or at least 1.0 wt. %, or at least 1.25 wt. %, and up to 10 wt. %, or up to 7 wt. %, or up to 5.0 wt. %, or up to 4 wt. %, or up to 3 wt. %; and a cumulative amount of AFFC, AFC, water and alcohol of less than 2 wt. %, or no more than 1.5 wt. %, or no more than 1.0 wt. %, or no more than 0.5 wt. %, or no more than 0.1 wt %; and desirably also AFC and AFFC in an amount of no more than 0.1 wt. %, or no more than 0.05 wt. %, or no more than 0.001 wt. %.

The concentration of DAFD in the partially purified liquid DAFD rich composition 721 is higher than the concentration of DAFD in the second liquid DAFD rich composition 711. The concentration of AFC in the partially purified liquid DAFD rich stream 721 is desirably depleted relative to the concentration of AFC in the second liquid DAFD rich composition 711 by a factor of at least 10×, or at least 100×, or at least 250×, or at least 500×, or at least 750×, or at least 1000×.

The temperature of the partially purified liquid DAFD rich stream effluent 721 from the AFC/AFFC removal zone 720 is desirably at least 220° C., or at least 230° C. and up to 270° C., or up to 260° C., or up to 250° C.

The partially purified liquid DAFD rich composition stream 721 is fed to an ACFC removal zone 730 to separate at least a portion of the DAFD from the partially purified liquid DAFD rich composition 721 using a physical separation process to produce a purified DAFD vapor composition 732 that is rich in the concentration of DAFD relative to the concentration of DAFD in the partially purified liquid DAFD rich composition 721, and a liquid ACFC bottoms stream 731 that is rich in the concentration of ACFC relative to the concentration of ACFC in the partially purified liquid DAFD rich composition 721, each by weight. Since the purified DAFD vapor composition 732 is rich in the concentration of DAFD relative to the concentration of DAFD in the partially purified liquid DAFD rich composition stream 721, it is necessarily also rich in the concentration of DAFD relative to the concentration of DAFD in the first liquid DAFD rich composition stream 620. Since the liquid ACFC bottoms stream 731 is rich in the concentration of ACFC relative to the concentration of ACFC in the partially purified liquid DAFD rich composition stream 721, it is necessarily also rich in the concentration of ACFC relative to the concentration of ACFC in the first liquid DAFD rich composition stream 620.

An example of a suitable physical separation apparatus is a distillation column. Suitable distillation pot temperatures range in zone 730 range from 200° C. to less than the boiling point of ACFC under the operating conditions. Desirably the temperature is set to at least the boiling point of the DAFD compound under the operating conditions. Suitable pot temperatures range from 210° C. to 280° C., or 220° C. to 260° C., or 230° C. to 255° C. The partially purified liquid DAFD rich composition 721 is desirably distilled at a vacuum to avoid degrading the DAFD product. The partially purified liquid DAFD rich composition 721 can be distilled at pressures ranging from 1 psia to atmospheric pressure. The column desirably has 10 to 70 trays, 10 to 60 trays to, or 10 to 50 trays, where a tray can be a valve tray, sieve tray, bubble cap tray, or an equivalent height of a packed bed. The distillation operating temperature desirably is set create a purified DAFD vapor composition and desirably to take off DAFD vapor as a distillate, which can optionally be partially or fully condensed and a portion returned to the column as reflux. The reflux ratio will vary with the number of trays and the mass of distillate produced.

The composition of the purified DAFD vapor stream 732 contains DAFD. The concentration of each these ingredients by weight based on the weight of the purified DAFD vapor stream is as follows:

DAFD: at least 99.0 wt. %, or at least 99.2 wt. %, or at least 99.5 wt. %, or at least 99.7 wt. %, or at least 99.8 wt. %, or at least 99.9 wt. %, and up to 99.999 wt. %, or up to 99.995 wt. %, or at least 99.99 wt. %; and ACFC, that if present at all, is present in an amount of greater than zero and not greater than 1000 ppm, or not greater than 100 ppm, or not greater than 10 ppm, or not greater than 1 ppm; and desirably AFFC, that if present at all, is present in an amount of greater than zero and not greater than 1000 ppm, or not greater than 100 ppm, or not greater than 50 ppm, or not greater than 20 ppm.

Optionally, this composition also contains very low amounts or no amount of: AFC, that if present at all, is present in an amount of not greater than 10 ppm, or not greater than 1 ppm, or not greater than 0.1 ppm; and alcohol, that if present at all, is present in an amount not greater than 10 ppm, or not greater than 1 ppm, or not greater than 0.1 ppm, and FDCA, if present at all, is present in an amount of not greater than 1000 ppm, or not greater than 100 ppm, or not greater than 10 ppm, or not greater than 1 ppm.

Desirably, if water is present, it is present in an amount of not greater than 1000 ppm, or not greater than 100 ppm, or not greater than 10 ppm.

The concentration of ACFC in the purified DAFD vapor stream 732 is depleted relative to the concentration of ACFC in the partially purified DAFD rich composition stream 721 by a factor of at least 10x, or at least 50x, or at least 100x, or at least 200x.

The composition of the ACFC liquid bottoms composition 731 contains ACFC and DAFD. The ACFC liquid bottoms composition comprises ACFC in an amount of at least 20 wt. %, or at least 30 wt. %, or at least 40 wt. % based on the weight of the ACFC liquid bottoms composition. The concentration of DAFD in the ACFC liquid bottoms composition desirably contains DAFD in an amount of less than 70 wt. %, or less than 50 wt. %, or less than 40 wt. %, or less than 30 wt. %, based on the weight of the ACFC liquid bottoms composition. The amount of ACFC by weight is desirably at least 1.5x, or at least 2.0x greater than the amount of DAFD in the ACFC liquid bottoms stream.

The concentration of ACFC in ACFC liquid bottoms composition 731 is desirably increased by a factor of at least 5x, or at least 10x, or at least 30x relative to the concentration of ACFC in the partially purified liquid DAFD rich composition 721.

The purified DAFD vapor composition is desirably condensed in a condenser to produce a purified liquid DAFD product composition containing liquefied DAFD at a temperature below the boiling point the DAFD compound and above its crystallization temperature at 1 atmosphere. The concentration of DAFD in the purified liquid DAFD product composition, based on the purified liquid DAFD product composition, is DAFD: at least 99.0 wt. %, or at least 99.2 wt. %, or at least 99.5 wt. %, or at least 99.7 wt. %, or at least 99.8 wt. %, or at least 99.9 wt. %, and up to 99.999 wt. %, or up to 99.995 wt. %, or at least 99.99 wt. %; and ACFC, that if present at all, is in an amount of not greater than 100 ppm, or not greater than 10 ppm, or not greater than 1 ppm; and desirably AFFC, that if present, is present in an amount of not more than 1000 ppm, or not more than 100 ppm, or not more than 50 ppm, or not more than 20 ppm, and optionally, AFC, that if present at all, is present in an amount of not greater than 10 ppm, or not greater than 1 ppm, or not greater than 0.1 ppm; and optionally, alcohol, that if present at all, is present in an amount not greater than 10 ppm, or not greater than 1 ppm, or not greater than 0.1 ppm; and desirably FDCA, if present at all, is present in an amount of not greater than 1000 ppm, or not greater than 100 ppm, or not greater than 10 ppm, or not greater than 1 ppm.

Desirably, if water is present in the purified liquid DAFD product composition, it is present in an amount of not greater than 1000 ppm, or not greater than 100 ppm, or not greater than 10 ppm, or not greater than 5 ppm, or not greater than 1 ppm. The solids concentration in the purified liquid DAFD product composition is desirably 0, but if solids are present, they are present in an amount of less than 0.1 wt %, or not more than 0.01 wt. %, or not more than 0.001 wt. %.

If desired, the purified liquid DAFD product composition can be hot. The hot purified liquid DAFD product composition can be routed to a molten product storage tank, to train tanker car or tanker truck capable of containing and transferring hot liquid material, and/or directly to a polyester process through a pipeline wherein DAFD is mixed with a polyester raw material comprising a diol such as ethylene glycol and reacted with said diol to form polymer comprising polyester.

Alternatively, the purified DAFD vapor composition can be condensed and crystallized to form DAFD solid particles comprising 99.9 wt. % DAFD on a solids basis as a slurry, or instead of a slurry, can be dried to form a dry DAFD solids stream, that in each case has a purity of at least the same purity levels as in the purified DAFD vapor rich stream 732. The conversion of the purified liquid DAFD composition into a dry solid stream can be accomplished by any other methods known in the art including a chilled belt flaker, spray drying, and the like. Thus, there is also provided a solids DAFD composition comprising solid particles of DAFD, wherein said solids comprise:

(i) at least 99.9 wt. % DAFD, or at least 99.95 wt. % DAFD, or at least 99.99 wt. % DAFD;

(ii) not more than 1000 ppm, or not more than 100 ppm, or not more than 10 ppm ACFC 5-(alkoxycarbonyl)furan-2-carboxylic acid, (iii) alkyl-5-formylfuran-2-carboxylate (AFFC) that if present, is present in an amount of not more than 1000 ppm, or not more than 100 ppm, or not more than 10 ppm, and optionally (iv) not more than 100 ppm, or not more than 100 ppm, or not more than 10 ppm, alkyl furan-2-carboxylate, and wherein the composition contains not more than 1 wt. % water, or not more than 0.5 wt. % water, or not more than 0.1 wt % water, or not more than 0.01 wt. % water. Desirably, the composition contains less than 1000 ppm furan dicarboxylic acid (FDCA), or less than 500 ppm FDCA, or less than 250 ppm FDCA, or less than 100 ppm FDCA, or less than 50 ppm FDCA, or less than 20 ppm FDCA, or less than 10 ppm FDCA, or less than 5 ppm FDCA, or less than 3 ppm FDCA.

The process of the invention is described in further detail in this example obtained by modeling using an ASPEN program:

For a given plant embodiment, a crude diester stream 510 is provided which comprises 199,628 kg methanol/day; 11,346 kg water/day; 508 kg MFC/day; 1,490 kg MFFC/day; 50,614 kg DMFD/day; 954 kg MCFC/day; and 479 kg FDCA impurities/day. The crude diester stream 510 is at a temperature of 230° C. and under a pressure of 2,000 psia. The crude diester stream is fed to a flash evaporation zone 600 where the pressure of the stream is reduced to 40 psia and by flash evaporation is split into two streams: an vapor alcohol stream 610 that comprises 164,502 kg methanol/day; 7,959 kg water/day; 87 kg MFC/day; 5 kg MFFC/day; and 134 kg DMFD/day; and a first liquid DAFD rich composition stream 620 which comprises 35,126 kg methanol/day; 3,387 kg water/day; 421 kg MFC/day; 1,485 kg MFFC/day; 50,480 kg DMFD/day; 954 kg MCFC/day; and 479 kg FDCA impurities/day.

The first liquid DAFD rich composition stream 620 is fed to a distillation column in the alcohol water removal zone 710 having 38 trays and set to a top pressure of 12 psia. The liquid bottoms temperature is 225° C. Methanol and water are removed as a second alcohol rich distillate stream 712 comprising 35,126 kg methanol/day; 3,338 kg water/day; and 18 kg MFC/day. The distillation column underflow liquid stream, the second liquid DAFD rich composition 711, comprises 49 kg water/day; 403 kg MFC/day; 1,485 kg MFFC/day; 50,480 kg DMFD/day; 954 kg MCFC/day; and 479 kg FDCA impurities/day.

The vapor alcohol stream 610 and second alcohol rich stream 712 are fed to a distillation column in the alcohol recovery zone 800 for alcohol recovery and water purge. The distillation column has 48 trays, is set at a top pressure of 8 psia, and has a liquid bottoms temperature of 95° C. The alcohol recycle distillate stream 802 comprises 199,627 kg methanol/day; and 1,122 kg water/day. The underflow water rich purge stream 801 comprises 10,174 kg water/day; 105 kg MFC/day; 5 kg MFFC/day; and 134 kg DMFD/day.

The second liquid DAFD rich stream 711 is fed to a distillation column in the AFC/AFFC removal zone 720. The distillation column has 48 trays, is set at a top pressure of 3 psia, and has a liquid bottoms temperature of 242° C. The column distillate stream, the AFC rich vapor composition 722, comprises 49 kg water/day; 403 kg MFC/day; 1,484 kg MFFC/day; 73 kg DMFD/day; and 9 kg FDCA impurities/day as a process purge of impurities. The column underflow stream, the partially purified liquid DAFD rich composition 721, comprises 1 kg MFFC/day; 50,480 kg DMFD/day; 954 kg MCFC/day; and 470 kg FDCA impurities/day.

The partially purified liquid DAFD rich composition stream 721 is fed to a distillation column in ACFC removal zone 730. The distillation column has 23 trays, is set at a top pressure of 1 psia, and has a liquid bottoms temperature of 248° C. The column distillate stream, the DAFD rich vapor 732, is the plant DMFD product stream and comprises 1 kg MFFC/day; 50,000 kg DMFD/day; 3 kg MCFC/day; and 5 kg FDCA impurities/day. The column underflow stream, ACFC liquid bottoms stream 731, comprises 408 kg DMFD/day; 951 kg MCFC/day; and 465 kg FDCA impurities/day.

The invention also includes a process for the manufacture of FDCA, which is one of the raw materials fed to the esterification zone 500. The process for the manufacture of FDCA will now be described in more detail.

The process comprises feeding an oxidizable composition to an oxidation zone, where the oxidizable composition contains a compound having a furan moiety. The furan moiety can be represented by the structure:

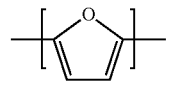

The compounds having a furan moiety are such that, upon oxidation, form carboxylic acid functional groups on the compound. Examples of compounds having furnan moieties include 5-(hydroxymethyl)furfural (5-HMF), and derivatives of 5-HMF. Such derivatives include esters of 5-HMF, such as those represented by the formula 5-R(CO)OCH$_2$-furfural where R=alkyl, cycloalkyl and aryl groups having from 1 to 8 carbon atoms, or 1-4 carbon atoms or 1-2 carbon atoms; ethers of 5-HMF represented by the formula 5-R'OCH$_2$-furfural, where R'=alkyl, cycloalkyl and aryl having from 1 to 8 carbon atoms, or 1-4 carbon atoms or 1-2 carbon atoms); 5-alkyl furfurals represented by the formula 5-R"-furfural, where R"=alkyl, cycloalkyl and aryl having from 1 to 8 carbon atoms, or 1-4 carbon atoms or 1-2 carbon atoms). Thus the oxidizable composition can contain mixtures of 5-HMF and 5-HMF esters; 5-HMF and 5-HMF ethers; 5-HMF and 5-alkyl furfurals, or mixtures of 5-HMF and its esters, ethers, and alkyl derivatives.

The oxidizable composition, in addition to 5-(hydroxymethyl)furfural (5-HMF) or an of its derivatives, may also contain 5-(acetoxymethyl)furfural (5-AMF) and 5-(ethoxymethyl)furfural (5-EMF).

Specific examples of 5-HMF derivatives include those having the following structures:

Preferred 5-HMF Derivative Feeds

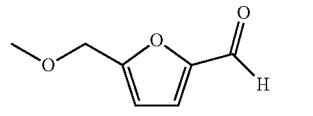

5-methoxymethylfurfural

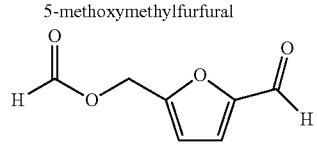

5-formoxymethylfurfural

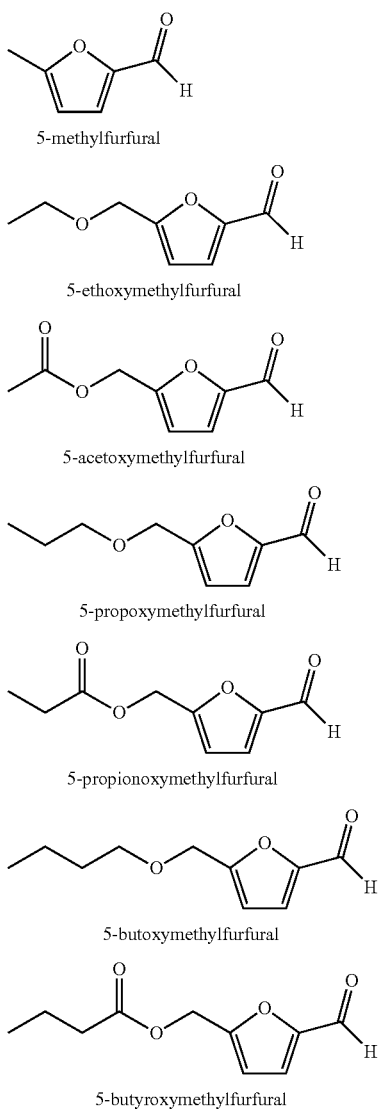

One embodiment is illustrated in FIG. 1. An oxidizable composition is fed to a primary oxidation zone 100 and reacted in the presence of a solvent, a catalyst system, and a gas comprising oxygen, to generate a crude dicarboxylic acid stream 110 comprising furan-2,5-dicarboxylic acid (FDCA).

For example, the oxidizable composition containing 5-HMF, or its derivatives, or combinations thereof, are oxidized with elemental $O_2$ in a multi-step reaction to form FDCA with 5-formyl furan-2-carboxylic acid (FFCA) as a key intermediate, represented by the following sequence:

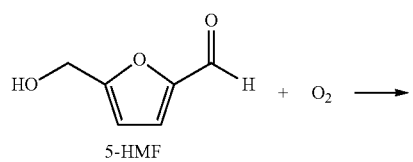

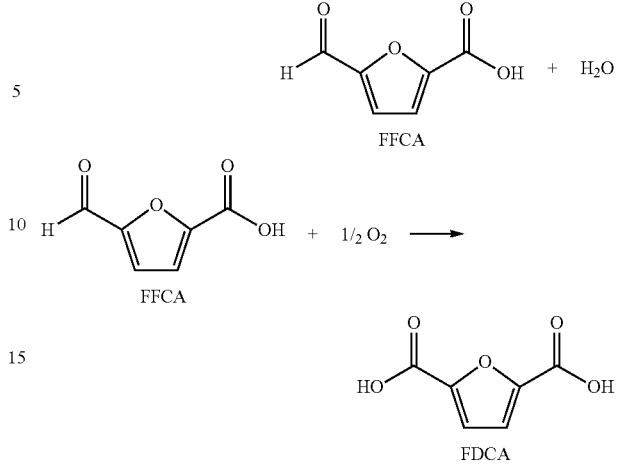

If desired, the oxygen gas stream 10 comprising oxygen, a solvent stream 30, and the oxidizable stream 20 can be fed to the primary oxidation zone 100 as separate streams. Or, an oxygen stream 10 comprising oxygen as one stream and an oxidizable stream 20 comprising solvent, catalyst, and oxidizable compounds as a second stream can be fed to the primary oxidation zone 100. Accordingly, the solvent, oxygen gas comprising oxygen, catalyst system, and oxidizable compounds can be fed to the primary oxidization zone 100 as separate and individual streams or combined in any combination prior to entering the primary oxidation zone 100 wherein these feed streams may enter at a single location or in multiple locations into the primary oxidizer zone 100.

The catalyst can be a homogenous catalyst soluble in the solvent or a heterogeneous catalyst. The catalyst composition is desirably soluble in the solvent under reaction conditions, or it is soluble in the reactants fed to the oxidation zone. Preferably, the catalyst composition is soluble in the solvent at 40° C. and 1 atm, and is soluble in the solvent under the reaction conditions.

Suitable catalysts components comprise at least one selected from, but are not limited to, cobalt, bromine and manganese compounds. Preferably a homogeneous catalyst system is selected. The preferred catalyst system comprises cobalt, manganese and bromine.

The cobalt atoms may be provided in ionic form as inorganic cobalt salts, such as cobalt bromide, cobalt nitrate, or cobalt chloride, or organic cobalt compounds such as cobalt salts of aliphatic or aromatic acids having 2-22 carbon atoms, including cobalt acetate, cobalt octanoate, cobalt benzoate, cobalt acetylacetonate, and cobalt naphthalate. The oxidation state of cobalt when added as a compound to the reaction mixture is not limited, and includes both the +2 and +3 oxidation states.

The manganese atoms may be provided as one or more inorganic manganese salts, such as manganese borates, manganese halides, manganese nitrates, or organometallic manganese compounds such as the manganese salts of lower aliphatic carboxylic acids, including manganese acetate, and manganese salts of beta-diketonates, including manganese acetylacetonate.

The bromine component may be added as elemental bromine, in combined form, or as an anion. Suitable sources of bromine include hydrobromic acid, sodium bromide, ammonium bromide, potassium bromide, and tetrabromoethane. Hydrobromic acid, or sodium bromide may be preferred bromine sources.

The amount of bromine atoms desirably ranges from at least 300 ppm, or at least 2000 ppm, or at least 2500 ppm, or at least 3000 ppm, or at least 3500 ppm, or at least 3750, ppm and up to 4500 ppm, or up to 4000 ppm, based on the weight of the liquid in the reaction medium of the primary oxidation zone. Bromine present in the an amount of 2500 ppm to 4000 ppm, or 3000 ppm to 4000 ppm are especially desirable to promote high yield.

The amount of cobalt atoms can range from at least 500 ppm, or at least 1500 ppm, or at least 2000 ppm, or at least 2500 ppm, or at least 3000 ppm, and up to 6000 ppm, or up to 5500 ppm, or up to 5000 ppm, based on the weight of the liquid in the reaction medium of the primary oxidation zone. Cobalt present in an amount of 2000 to 6000 ppm, or 2000 to 5000 ppm are especially desirable to promote high yield.

The amount of manganese atoms can range from 2 ppm, or at least 10 ppm, or at least 30 ppm, or at least 50 ppm, or at least 70 ppm, or at least 100 ppm, and in each case up to 600 ppm, or up to 500 ppm or up to 400 ppm, or up to 350 ppm, or up to 300 ppm, or up to 250 ppm, based on the weight of the liquid in the reaction medium of the primary oxidation zone. Manganese present in an amount ranging from 30 ppm to 400 ppm, or 70 ppm to 350 ppm, or 100 ppm to 350 ppm is especially desirable to promote high yield.

The weight ratio of cobalt atoms to manganese atoms in the reaction mixture can be from 1:1 to 400:1, or 10:1 to about 400:1. A catalyst system with improved Co:Mn ratio can lead to high yield of FDCA. To increase the yield of FDCA, when the oxidizable composition fed to the oxidation reactor comprises 5-HMF, then the cobalt to manganese weight ratio is at least 10:1, or at least 15:1, or at least 20:1, or at least 25:1, or at least 30:1, or at least 40:1 or at least 50:1, or at least 60:1, and in each case up to 400:1. However, in the case where the oxidizable composition comprises esters of 5-HMF, ethers of 5-HMF, or 5-alkyl furfurals, or mixtures of any of these compounds together or with 5-HMF, the cobalt to manganese weight ratio can be lowered while still obtaining high yield of FDCA, such as a weight ratio of Co:Mn of at least 1:1, or at least 2:1, or at least 5:1, or at least 9:1, or at least 10:1, or at least 15:1, or at least 20:1, or at least 25:1, or at least 30:1, or at least 40:1, or at least 50:1, or at least 60:1 and in each case up to 400:1.

The weight ratio of cobalt atoms to bromine atoms is desirably at least 0.7:1, or at least 0.8:1, or at least 0.9:1, or at least 1:1,or at least 1.05:1, or at least 1.2:1,or at least 1.5:1,or at least 1.8:1,or at least 2:1,or at least 2.2:1,or at least 2.4:1,or at least 2.6:1,or at least 2.8:1,and in each case up to 3.5, or up to 3.0, or up to 2.8.

The weight ratio of bromine atoms to manganese atoms is from about 2:1 to 500:1.

Desirably, the weight ratio of cobalt to manganese is from 10:1 to 400:1, and the weight ratio of cobalt to bromine atoms ranges from 0.7:1 to 3.5:1. Such a catalyst system with improved Co:Mn and Co:Br ratio can lead to high yield of FDCA (minimum of 90%), decrease in the formation of impurities (measured by b*) causing color in the downstream polymerization process while keeping the amount of CO and $CO_2$ (carbon burn) in the off-gas at a minimum.

Desirably, the amount of bromine present is at least 1000 ppm and up to 3500 ppm, and the weight ratio of bromine to manganese is from 2:1 to 500:1. This combination has the advantage of high yield and low carbon burn.

Desirably, the amount of bromine present is at least 1000 ppm and up to 3000 ppm, and the amount of cobalt present is at least 1000 ppm and up to 3000 ppm, and the weight ratio of cobalt to manganese is from 10:1 to 100:1. This combination has the advantage of high yield and low carbon burn.

Suitable solvents include aliphatic solvents. In an embodiment of the invention, the solvents are aliphatic carboxylic acids which include, but are not limited to, $C_2$ to $C_6$ monocarboxylic acids, e.g., acetic acid, propionic acid, n-butyric acid, isobutyric acid, n-valeric acid, trimethylacetic acid, caprioic acid, and mixtures thereof.

The most common solvent used for the oxidation is an aqueous acetic acid solution, typically having a concentration of 80 to 99 wt. %. In especially preferred embodiments, the solvent comprises a mixture of water and acetic acid which has a water content of 0% to about 15% by weight. Additionally, a portion of the solvent feed to the primary oxidation reactor may be obtained from a recycle stream obtained by displacing about 80 to 90% of the mother liquor taken from the crude reaction mixture stream discharged from the primary oxidation reactor with fresh, wet acetic acid containing about 0% to 15% water.

The oxidizing gas stream comprises oxygen. Examples include, but are not limited to, air and purified oxygen. The amount of oxygen in the primary oxidation zone ranges from about 5 mole % to 45 mole %, 5 mole % to 60 mole %, or 5 mole % to 80 mole %.

The temperature of the reaction mixture in the primary oxidation zone can vary from about 100° C. to about 220° C. The temperature of the reaction mixture in the primary oxidation zone is at least 100° C., or at least 105° C., or at least 110° C., or at least 115° C., or at least 120° C., or at least 125° C., or at least 130° C., or at least 135° C., or at least 140° C., or at least 145° C., or at least 150° C., or at least 155° C., or at least 160° C., and can be as high as 220° C., or up to 210° C., or up to 200° C., or up to 195° C., or up to 190° C., or up to 180° C., or up to 175° C., or up to 170° C., or up to 165° C., or up to 160° C., or up to 155° C., or up to 150° C., or up to 145° C., or up to 140° C., or up to 135° C., or up to 130° C. In other embodiments, the temperate ranges from 105° C. to 180° C., or from 105° C. to 175° C., or from 105° C. to 160° C., or from 105° C. to 165° C., or from 105° C. to 160° C., or from 105° C. to 155° C., or from 105° C. to 150° C., or from 110° C. to 180° C., or from 110° C. to 175° C., or from 110° C. to 170° C., or from 110° C. to 165° C., or from 110° C. to 160° C., or from 110° C. to 155° C., or from 110° C. to 150° C., or from 110° C. to 145° C., or from 115° C. to 180° C., or from 115° C. to 175° C., or from 115° C. to 170° C., or from 115° C. to 167° C., or from 115° C. to 160° C., or from 115° C. to 155° C., or from 110° C. to 150° C., or from 115° C. to 145° C., or from 120° C. to 180° C., or from 120° C. to 175° C., or from 120° C. to 170° C., or from 120° C. to 165° C., or from 120° C. to 160° C., or from 120° C. to 155° C., or from 120° C. to 150° C., or from 120° C. to 145° C., or from 125° C. to 180° C., or from 125° C. to 175° C., or from 125° C. to 170° C., or from 125° C. to 165° C., or from 125° C. to 160° C., or from 125° C. to 155° C., or from 125° C. to 150° C., or from 125° C. to 145° C., or from 130° C. to 180° C., or from 130° C. to 175° C., or from 130° C. to 170° C., or from 130° C. to 165° C., or from 130° C. to 160° C., or from 130° C. to 155° C., or from 130° C. to 150° C., or from 130° C. to 145° C., or from 135° C. to 180° C., or from 135° C. to 175° C., or from 135° C. to 170° C., or from 135° C. to 170° C., or from 135° C. to 165° C., or from 135° C. to 160° C., or from 135° C. to 155° C., or from 135° C. to 150° C., or from 135° C. to 145° C., or from 140° C. to 180° C., or from 140° C. to 175° C., or from 140° C. to 170° C., or from 140°

C. to 170° C., or from 140° C. to 165° C., or from 140° C. to 160° C., or from 140° C. to 155° C., or from 140° C. to 150° C., or from 140° C. to 145° C., or from 145° C. to 180° C., or from 145° C. to 175° C., or from 145° C. to 170° C., or from 145° C. to 170° C., or from 145° C. to 165° C., or from 145° C. to 160° C., or from 145° C. to 155° C., or from 145° C. to 150° C., or from 150° C. to 180° C., or from 150° C. to 175° C., or from 150° C. to 170° C., or from 150° C. to 165° C., or from 150° C. to 160° C., or from 150° C. to 155° C., or from 155° C. to 180° C., or from 155° C. to 175° C., or from 155° C. to 170° C., or from 155° C. to 165° C., or from 155° C. to 160° C., or from 160° C. to 180° C., or from 160° C. to 175° C., or from 160° C. to 170° C., or from 160° C. to 165° C., or from 165° C. to 180° C., or from 165° C. to 175° C., or from 165° C. to 170° C., or from 165° C. to 180° C., or from 165° C. to 175° C., or from 165° C. to 170° C., or from 170° C. to 180° C., or from 170° C. to 175° C., or from 175° C. to 180° C.

To minimize carbon burn, it is desired that the temperature of the reaction mixture is not greater than 165° C., or not greater than 160° C. In the process of the invention, the contents of the oxidizer off gas comprise COx, wherein x is 1 or 2, and the amount of COx in the oxidizer off gas is less than 0.05 moles of COx per mole of the total oxidizable feed to the reaction medium, or no more than 4 moles of COx per mole of the total oxidizable feed to the reaction medium, or no more than 6 moles of COx per mole of the total oxidizable feed to the reaction medium. The carbon burn as determined by the COx generation rate can be calculated as follows: (moles of CO+ moles of CO2)/moles of oxidizable feed. The low carbon burn generation rate in the process of the invention is achievable by the combination of low reaction temperature, and the molar weight ratios of the catalyst components as described above.

The oxidation reaction can be conducted under a pressure ranging from 40 to 300 psia. A bubble column is desirably operated under a pressure ranging from 40 psia to 150 psia. In a stirred tank vessel, the pressure is desirably set to 100 psia to 300 psia.

Oxidizer off gas stream 120 containing COx (CO and $CO_2$), water, nitrogen, and vaporized solvent, is routed to the oxidizer off gas treatment zone 1000 to generate an inert gas stream 810, liquid stream 820 comprising water, and a recovered oxidation solvent stream 830 comprising condensed solvent. In one embodiment, oxidizer off gas stream 120 can be fed to directly, or indirectly after separating condensables such as solvent from non-condensables such as COx and nitrogen in a separation column (e.g. distillation column with 10-200 trays), to an energy recovery device such as a turbo-expander to drive an electric generator. Alternatively or in addition, the oxidizer off gas stream can be fed to a steam generator before or after the separation column to generate steam, and if desired, may then be fed to a turbo-expander and pre-heated prior to entry in the expander if necessary to ensure that the off gas does not condense in the turbo-expander.

In another embodiment, at least a portion of the oxidation solvent stream 830 recovered from the oxidizer off-gas stream is routed to a filter and then to a wash solvent stream 320 to become a portion of the wash solvent stream 320 for the purpose of washing the solids present in the solid-liquid separation zone. In another embodiment, the inert gas stream 810 can be vented to the atmosphere. In yet another embodiment, at least a portion of the inert gas stream 810 can be used as an inert gas in the process for inerting vessels and or used for convey gas for solids in the process.

The oxidation can be conducted in a continuous stirred tank reactor or in a bubble column reactor.

The FDCA formed by the oxidation reaction desirably precipitates out of the reaction mixture. The reaction mixture comprises the oxidizable composition, solvent, and catalyst if a homogeneous catalyst is used, otherwise it comprises the oxidizable composition and solvent.

The product of the oxidation reaction is a crude dicarboxylic acid stream 110 comprising FDCA as a solid, FDCA dissolved in the solvent, solvent, and by-products and intermediate products, and homogeneous catalyst system if used. Examples of by-products include levulinic acid, succinic acid, and acetoxy acetic acid. Examples of intermediate products include 5-formyl furan-2-carboxylic acid (FFCA) and 2,5-diformylfuran.

The percent solids in the crude dicarboxylic acid stream ranges is at least 10 wt %, or at least 15 wt. %, or at least 20 wt. %, or at least 25 wt. %, or at least 28 wt. %, or at least 30 wt. %, or at least 32 wt. %, or at least 35 wt. %, or at least 37 wt. %, or at least 40 wt. %. While there is no upper limit, as a practice the amount will not exceed 60 wt. %, or no greater than 55 wt. %, or no greater than 50 wt. %, or no greater than 45 wt. %, or not greater than 43 wt. %, or not greater than 40 wt %, or not greater than 39 wt %. Of the solids in the crude dicarboxylic acid stream, it is desirable that at least 80 wt. %, or at least 85 wt. %, or at least 90 wt. %, or at least 95 wt. % of the solids in each case is FDCA.

The stated amount of each of the following intermediates, product, and impurities are based on the weight of the solids in the crude carboxylic acid composition produced in the primary oxidation reactor in the oxidation zone 100.

The amount of the intermediate FFCA present in the crude dicarboxylic acid stream is not particularly limited. Desirably, the amount is less than 4 wt. %, or less than 3.5 wt. %, or less than 3.0 wt. %, or less than 2.5 wt. %, or up to 2.0 wt. %, or up to 1.5 wt. %, or up to 1.0 wt. %, or up to 0.8 wt. %, based on the weight of the solids present in the crude dicarboxylic acid stream.

Impurities, if present in the crude dicarboxylic acid composition, include such compounds as 2,5-diformylfuran, levulinic acid, succinic acid, and acetoxy acetic acid. These compounds can be present, if at all, in an amount of 0 wt % to about 0.2 wt % 2,5 difrmylfuran, levulinic acid in an amount ranging from 0 wt % to 0.5 wt %, succinic acid in an amount ranging from 0 wt % to 0.5 wt % and acetoxy acetic acid in an amount ranging from 0 wt % to 0.5 wt %, and a cumulative amount of these impurities in an amount ranging from 0 wt. % to 1 wt. %, or from 0.01 wt % to 0.8 wt. %, or from 0.05 wt % to 0.6 wt. %, each based on the weight of the solids present in the crude dicarboxylic acid stream.

In another embodiment of the invention the crude dicarboxylic acid composition 110 comprises FDCA, FFCA and 5-(ethoxycarbonyl)furan-2-carboxylic acid ("EFCA"). The EFCA in the crude dicarboxylic acid composition 110 can be present in an amount of at least 0.05 wt %, or at least 0.1 wt %, or at least 0.5 wt % and in each case up to about 4 wt %, or up to about 3.5 wt %, or up to 3 wt. %, or up to 2.5 wt %, or up to 2 wt. %, based on the weight of the solids present in the crude dicarboxylic acid stream.

The yield of FDCA, on a solids basis and measured after the drying zone step, is at least 60%, or at least 65%, or at least 70%, or at least 72%, or at least 74%, or at least 76%, or at least 78%, or at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 95%, and up to 99%, or up to 98%, or up to 97%, or up to 96%, or up to 95%, or up to 94%, or up to 93%, or up to 92%, or up to 91%, or up to 90%, or up to 89%. For example, the yield can range from 70% up to 99%, or 74% up to 98%, or 78% up to 98%, or 80% up to 98%, or 84% up to 98%, or 86% up to 98%, or 88% up to 98%, 90% up to 98%, or 91% up to 98%, or 92% up to 98%, or 94% up to 98%, or 95% up to 99%.

Yield is defined as mass of FDCA obtained divided by the theoretical amount of FDCA that should be produced based on the amount of raw material use. For example, if one mole or 126.11 grams of 5-HMF are oxidized, it would theoretically generate one mole or 156.01 grams of FDCA. If for example, the actual amount of FDCA formed is only 150 grams, the yield for this reaction is calculated to be=(150/156.01) times 100, which equals a yield of 96%. The same calculation applies for oxidation reaction conducted using 5-HMF derivatives or mixed feeds.

The maximum b* of the dried solids, or wet cake, is not particularly limited. However, a b* of not more than 20, or no more than 19, or no more than 18, or no more than 17, or no more than 16, or no more than 15, or no more than 10, or no more than 8, or no more than 6, or no more than 5, or no more than 4, or no more than 3, is desirable without having to subject the crude carboxylic acid composition to hydrogenation. However, if lowered b* is important for a particular application, the crude carboxylic acid composition can be subjected to hydrogenation.

The b* is one of the three-color attributes measured on a spectroscopic reflectance-based instrument. The color can be measured by any device known in the art. A Hunter Ultrascan XE instrument is typically the measuring device. Positive readings signify the degree of yellow (or absorbance of blue), while negative readings signify the degree of blue (or absorbance of yellow).

In the next step, which is an optional step, the crude dicarboxylic acid stream 110 can fed to a cooling zone 200 to generate a cooled crude dicarboxylic acid slurry stream 210 and a $1^{st}$ solvent vapor stream 220 comprising solvent vapor. The cooling of crude carboxylic slurry stream 110 can be accomplished by any means known in the art. Typically, the cooling zone 200 is a flash tank. All or a portion of the crude dicarboxylic acid stream 110 can be fed to the cooling zone.

All or a portion of the crude dicarboxylic acid stream 110 can be fed to solid-liquid separation zone 300 without first being fed to a cooling zone 200. Thus, none or only a portion can be cooled in cooling zone 200. The temperature of stream 210 exiting the cooling zone can range from 35° C. to 160° C., 55° C. to 120° C., and preferably from 75° C. to 95° C.

The crude dicarboxylic acid stream 110, or 210 if routed through a cooling zone, is fed to a solid-liquid separation zone 300 to generate a crude carboxylic acid wet cake stream 310 comprising FDCA. The functions of isolating, washing and dewatering the crude carboxlic acid stream may be accomplished in a single solid-liquid separation device or multiple solid-liquid separation devices. The solid-liquid separation zone 300 comprises at least one solid-liquid separation device capable of separating solids and liquids, washing solids with a wash solvent stream 320, and reducing the % moisture in the washed solids to less than 30 weight %. Desirably, the solid-liquid separation device is capable of reducing the % moisture down to less than 20 weight %, or less than 15 weight %, and preferably 10 weight % or less. Equipment suitable for the solid liquid separation zone can typically be comprised of, but not limited to, the following types of devices: centrifuges of all types including but not limited to decanter and disc stack centrifuges, solid bowl centrifuges, cyclone, rotary drum filter, belt filter, pressure leaf filter, candle filter, and the like. The preferred solid liquid separation device for the solid liquid separation zone is a continuous pressure drum filter, or more specifically a continuous rotary pressure drum filter. The solid-liquid separator may be operated in continuous or batch mode, although it will be appreciated that for commercial processes, the continuous mode is preferred.

The temperature of crude carboxylic acid slurry stream, if cooled as stream 210, fed to the solid-liquid separation zone 300 can range from 35° C. to 160° C., 55° C. to 120° C., and is preferably from 75° C. to 95° C.

The wash stream 320 comprises a liquid suitable for displacing and washing mother liquor from the solids. For example, the wash solvent comprises acetic acid, or acetic acid and water, an alcohol, or water, in each case up to an amount of 100%. The temperature of the wash solvent can range from 20° C. to 180° C., or 40° C. and 150° C., or 50° C. to 130° C. The amount of wash solvent used is defined as the wash ratio and equals the mass of wash divided by the mass of solids on a batch or continuous basis. The wash ratio can range from about 0.3 to about 5, about 0.4 to about 4, and preferably from about 0.5 to 3.

There can be multiple washes with the same wash solvent or with different wash solvents. For example a first wash comprising acetic acid may be followed by a second wash comprising the alcohol utilized in the downstream esterification reaction zone.

After solids are washed in the solid liquid separation zone 300, they are dewatered. Dewatering can take place in the solid liquid separation zone or it can be a separate device from the solid-liquid separation device. Dewatering involves reducing the mass of moisture present with the solids to less than 30% by weight, less than 25% by weight, less than 20% by weight, and most preferably less than 15% by weight so as to generate a crude carboxylic acid wet cake stream 310 comprising FDCA. Dewatering can be accomplished in a filter by passing a gas stream through the solids to displace free liquid after the solids have been washed with a wash solvent. Alternatively, dewatering can be achieved by centrifugal forces in a perforated bowl or solid bowl centrifuge.

One or more washes may be implemented in solid-liquid separation zone 300. One or more of the washes, preferably at least the final wash, in solid-liquid separation zone 300 comprises a hydroxyl functional compound as defined further below, such as an alcohol (e.g. methanol). By this method, a wet cake stream 310 is produced comprising the hydroxyl functional compound such as methanol in liquid form. The amount of the hydroxyl functional compound in liquid form in the wet cake can be at least 50 wt %, or at least 75 weight %, or at least 85% weight %, or at least 95 weight % hydroxyl functional compound such as methanol based on the weight of the liquids in the wet cake stream. The advantage of adopting this technique of washing with a hydroxyl functional compound is that a portion or all of the wet cake can be fed to the esterification zone 500 without undergoing, or by-pass, a step of feeding the wet cake to a vessel for drying the wet cake in a drying zone 400 after the solid-liquid separation zone.

In one embodiment, 100% of wet cake stream 310 is fed to esterification reaction zone 500 without undergoing or subjecting the wet cake to a vessel for drying the wet cake from the solid liquid separation zone 300.

Stream 330 generated in solid-liquid separation zone 300 is a liquid mother liquor stream comprising oxidation solvent, catalyst, and impurities. If desired, a portion of mother liquor stream 330 can be fed to a purge zone 900 and a portion can be fed back to the primary oxidation zone 100, wherein a portion is at least 5 weight % based on the weight of the liquid. Wash liquor stream 340 is also generated in the solid-liquid separation zone 300 and comprises a portion of the mother liquor present in stream 210 and wash solvent wherein the weight ratio of mother liquor mass to wash solvent mass in the wash liquor stream is less than 3 and preferably less than 2. From 5% to 95%, from 30% to 90%, and most preferably from 40 to 80% of mother liquor present in the crude carboxylic acid stream fed to the solid-liquid separation zone 200 is isolated in solid-liquid separation zone 300 to generate mother liquor stream 330 resulting in dissolved matter comprising impurities present in the displaced mother liquor not going forward in the process. The mother liquor stream 330 contains dissolved impurities removed from the crude dicarboxylic acid.

Sufficient hydroxyl functional compound such as an alcohol (e.g. methanol) is fed to the solid liquid separation zone 300 that becomes mixed with solids present resulting in a low impurity slurry stream 310 being pumpable with weight % solids ranging from 1% to 50%, 10% to 40%, and preferably the weight % solids in stream 310 will range from 25% to 38%.

In one embodiment, from 5% to 100% by weight of the displaced mother liquor stream 330 is routed to a purge zone 900 wherein a portion of the impurities present in stream 330 are isolated and exit the process as purge stream 920, wherein a portion is 5% by weight or greater. Recovered solvent stream 910 comprises solvent and catalyst isolated from stream 330 and is recycled to the process. The recovered solvent stream 910 can be recycled to the primary oxidation zone 100 and contains greater than 30% of the catalyst that entered the purge zone 900 in stream 330. The stream 910 recycled to the primary oxidation zone 100 may contain greater than 50 weight %, or greater than 70 weight %, or greater than 90 weight % of the catalyst that enters the purge zone 900 in stream 330 on a continuous or batch basis.

Optionally, a portion up to 100% of the crude carboxylic acid composition may be routed directly to a secondary oxidation zone (not shown) before being subjected to a solid liquid separation zone 300.

Generally, oxidation in a secondary oxidation zone is at a higher temperature than the oxidation in the primary oxidation zone 100 to enhance the impurity removal. In one embodiment, the secondary oxidation zone is operated at about 30° C., 20° C., and preferably 10° C. higher temperature than the oxidation temperature in the primary oxidation zone 100 to enhance the impurity removal. The secondary oxidation zone can be heated directly with solvent vapor, or steam via stream or indirectly by any means known in the art.

Additional purification of the crude carboxylic acid stream can be accomplished in the secondary oxidation zone by a mechanism involving recrystallization or crystal growth and oxidation of impurities and intermediates including FFCA. One of the functions of the secondary oxidation zone is to convert FFCA to FDCA. FFCA is considered monofunctional relative to a polyester condensation reaction because it contains only one carboxylic acid. FFCA is present in the crude carboxylic acid composition stream. FFCA is generated in the primary oxidation zone 100 because the reaction of 5-HMF to FFCA can be about eight times faster than the reaction of FFCA to the desired di-functional product FDCA. Additional air or molecular oxygen may be fed to the secondary oxidation zone in an amount necessary to oxidize a substantial portion of the partially oxidized products such as FFCA to the corresponding carboxylic acid FDCA. Generally, at least 70% by weight, or at least 80 wt %, or at least 90 wt % of the FFCA present in the crude carboxylic acid composition exiting the primary oxidation zone can be converted to FDCA in the secondary oxidation zone. Significant concentrations of monofunctional molecules like FFCA in the dried, purified FDCA product are particularly detrimental to polymerization processes as they may act as chain terminators during the polyester condensation reaction.

If a secondary oxidation zone is employed, the secondary oxidation slurry can be crystallized to form a crystallized slurry stream. Vapor from the crystallization zone can be condensed in at least one condenser and returned to the crystallization zone or recycled, or it can be withdrawn or sent to an energy recovery device. The crystallizer off-gas can be removed and routed to a recovery system where the solvent is removed, and crystallizer off gas containing VOC's may be treated, for example, by incineration in a catalytic oxidation unit. The crystallizer can be operated by cooling the secondary oxidation slurry to a temperature between about 40° C. to about 175° C. to form a crystallized slurry stream.

The crystallized slurry stream can then be subjected to a cooling zone 200 if desired and the process continued as described above.

Instead of using a wet cake, one may produce a dried solid. The wet cake produced in the solid liquid separation zone 300 can be dried in a drying zone 400 to generate a dry purified carboxylic acid solid 410 and a vapor stream 420. The vapor stream 420 typically comprises the wash solvent vapor used in the solid liquid separation zone, and may additionally contain the solvent used in the primary oxidation zone. The drying zone 400 comprises at least one dryer and can be accomplished by any means known in the art that is capable of evaporating at least 10% of the volatiles remaining in the purified wet cake stream to produce the dried, purified carboxylic acid solids. For example, indirect contact dryers include, but are not limited to, a rotary steam tube dryer, a Single Shaft Porcupine dryer, and a Bepex Solidaire dryer. Direct contact dryers include, but are not limited to, a fluid bed dryer and drying in a convey line.

The dried, purified carboxylic acid solids comprising purified FDCA can be a carboxylic acid composition with less than 8% moisture, preferably less than 5% moisture, and more preferably less than 1% moisture, and even more preferably less than 0.5%, and yet more preferably less than 0.1%.

A vacuum system can be utilized to draw vapor stream 420 from the drying zone 400. If a vacuum system is used in this fashion, the pressure at the dryer outlet can range from about 760 mmHg to about 400 mmHg, from about 760 mmHg to about 600 mmHg, from about 760 mmHg to about 700 mmHg, from about 760 mmHg to about 720 mmHg, and from about 760 mmHg to about 740 mmHg wherein pressure is measured in mmHg above absolute vacuum.

The dried, purified carboxylic acid solids, or the solids in the wet cake, desirably have a b* less than about 9.0, or less than about 6.0, or less than about 5.0, or less than about 4.0. or less than about 3.

It should be appreciated that the process zones previously described can be utilized in any other logical order to produce the dried, purified carboxylic acid. It should also be appreciated that when the process zones are reordered that the process conditions may change. It is also understood that all percent values are weight percents.

One function of drying zone 400 is to remove by evaporation oxidation solvent comprising a mono-carboxylic acid with 2 to 6 carbons that can be present in the crude carboxylic acid wet cake stream 310. The % moisture in crude carboxylic acid wet cake stream 310 typically ranges from 4.0% by weight to 30% by weight depending on the operation conditions of the solid-liquid separation zone 300. If for example, the liquid portion of stream 310 is about 90% acetic acid, the amount of acetic acid present in stream 310 can range from about 3.6 weight % to 27 weight %. It is desirable to remove acetic acid prior to esterification zone 500 because acetic acid will react with the alcohol present in the zone 500 to create unwanted by products. For example, if methanol is fed to esterification zone 500 for the purpose of reacting with FDCA, it will also react with acetic acid present to form methyl acetate and therefore consume methanol and generate an unwanted by-product. It is desirable to minimize the acetic acid content of the crude carboxylic acid stream comprising FDCA that is fed to esterification zone 500 to less than 3.6 weight %, preferably less than 1 weight %, and more preferably less than 0.5 weight %, and most preferably less than 0.1 weight %. One method for achieving this is to dry a crude carboxylic acid wet cake stream 310 comprising acetic acid prior to routing the crude carboxylic to esterification zone 500. Another method for minimizing the oxidation solvent comprising mono-carboxylic acid with carbons ranging from 2 to 5 in the crude carboxylic acid stream 410 routed to esterification zone 500 to an acceptable level without utilizing a dryer zone 400 is to conduct non-monocarboxylic acid wash or washes in solid-liquid separation zone 300 to wash the oxidation solvent from the solids with a wash comprising any wash solvent compatible with the esterification zone 500 chemistry to generate a crude carboxylic acid wet cake stream 310 suitable for routing directly to esterification zone 500 without being dried in drying zone 400. Acceptable wash solvents comprise solvents that do not make undesirable by products in esterification zone 500. For example, water is an acceptable wash solvent to displace acetic acid from solids in solid-liquid separation zone 300. Another acceptable wash solvent is an alcohol that will be used as a reactant in the esterification zone 500. There can be multiple and separate washes in the solid liquid separation zone 300. A wash feed can comprise water up to 100 weight %. A wash feed can comprise an alcohol up to 100 weight %. A wash feed can comprise methanol up to 100%. A wash feed can comprise the same alcohol utilized in the esterification zone 500 for reaction with FDCA to form the di-ester product. In one embodiment, a wet cake dewatering step can be used after the wet cake is formed in the solid liquid separation zone 300 and before any non-acetic acid wash is employed. This dewatering step will minimize the liquid content of the wet cake prior to washing with a non-acetic acid wash solvent such as water and or methanol as described above, thus minimizing the cost to separate any mixtures of acetic acid and non-acetic acid wash solvents that are generated in solid-liquid separation zone 300.

The solid dicarboxylic acid composition 410, which can be either dried carboxylic acid solids or wet cake, comprising FDCA, and the alcohol composition stream 520 are fed to the esterification reaction zone 500. The solid dicarboxylic acid composition 410 can be shipped via truck, ship, or rail as solids. However, an advantage of the invention is that the process for the oxidation of the oxidizable material containing the furan group can be integrated with the process for the manufacture of the crude diester composition.

An integrated process includes co-locating the two manufacturing facilities, one for oxidation and the other for esterification, within 10 miles, or within 5 miles, or within 2 miles, or within 1 mile, or within ½ mile of each other. An integrated process also includes having the two manufacturing facilities in solid or fluid communication with each other. If a solid dicarboxylic acid composition is produced, the solids can be conveyed by any suitable means, such as air or belt, to the esterification facility. If a wet cake dicarboxylic acid composition is produced, the wet cake can be moved by belt or pumped as a liquid slurry to the facility for esterification.

EXAMPLES

This invention can be further illustrated by the following examples of embodiments thereof, although it will be understood that these examples are included merely for the purposes of illustration and are not intended to limit the scope of the invention unless otherwise specifically indicated.

Example 1

6.5 g of crude FFCA and 43.7 g of MeOH were mixed in a clean and dry 100 mL autoclave at a molar ratio of methanol to FDCA of 30. The autoclave mixture was heated to 100° C. in a closed system and let the pressure develop. After 6 h at 100° C. the reaction mixture was cooled to room temperature. A liquid product was obtained. GC analysis of the liquid product showed the following composition: 14.05 wt % of DMFCA based on the weight of reaction product, 1.33 wt % of MDMFC based on the weight of product, 79.53 wt % of methanol based on the weight of product, and 2.26 wt % of water.

Example 2

Example 1 was repeated at 170° C. for 6 h. GC analysis of the liquid product showed the following composition: 2.81 wt % of DMFCA based on the weight of reaction product, 14.79 wt % of MDMFC based on the weight of product, 78.91 wt % of methanol based on the weight of product, and 3.36 wt % of water.

Example 3

Example 1 was repeated at 200° C. for 6 h. GC analysis of the liquid product showed the following composition: 0.81 wt % of DMFCA based on the weight of reaction product, 16.19 wt % of MDMFC based on the weight of product, 74.08 wt % of methanol based on the weight of product, and 4.15 wt % of water.

Gas Chromatographic Method

Process samples were analyzed using a Shimadzu gas chromatograph Model 2010 (or equivalent) equipped with a split/heated injector (300° C.) and a flame ionization detector (300° C.). A capillary column (60 meter×0.32 mm ID) coated with (6% cyanopropylphenyl)-methylpolysiloxane at 1.0 tm film thickness (such as DB-1301 or equivalent) was employed. Helium was used as the carrier gas with an initial column head pressure of 29.5 psi and an initial column flow of 3.93 mL/minute while the carrier gas linear velocity of 45 cm! second was maintained constant throughout the entire oven temperature program. The column temperature was programmed as follows: The initial oven temperature was set at 80° C. and was held for 6 minutes, the oven was ramped up to 150° C. at 4° C./minute and was held at 150° C. for 0 minute, the oven was ramped up to 240° C. at 10° C./minute and was held at 240° C. for 5 minutes, then the oven was ramped up to 290° C. at 10° C./minute and was held at 290° C. for 17.5 minutes (the total run time was 60 mins). 1.0-gl of the prepared sample solution was injected with a split ratio of 40:1. EZ-Chrom Elite chromatography data system software was used for data acquisition and data processing. The sample preparation was done by weighing 0.1 g (accurate to 0.1 mg) of sample in a GC vial and adding 200.0 µl ISTD solution (1% by volume of decane in pyridine) and 1000 µl of BSTFA (N, O-bis(trimethylsilyl) trifluoroacetamide) with 1% TMSC1 (trimethylchlorosilane) to the GC vial. The content was heated at 80° C. for 30 minutes to ensure complete derivatization. 1.0 µl of this prepared sample solution was injected for GC analysis.

What I claim is:

1. A dialkyl-furan-2,5-dicarboxylate (DAFD) composition comprising solid particles of DAFD, wherein said composition comprises:
   (i) at least 98 wt. % of DAFD;
   (ii) 5-(alkoxycarbonyl)furan-2-carboxylic acid (ACFC) that if present, is present in an amount of not more than 1000 ppm, and
   (iii) alkyl-5-formylfuran-2-carboxylate (AFFC) that if present, is present in an amount of not more than 1000 ppm,
   wherein
   (iv) 5-(dialkoxymethyl)furan-2-carboxylic acid (DAFCA) is present in an amount of not more than 1000 ppm, and
   (v) alkyl 5-(dialkoxymethyl)furan-2-carboxylate (ADAFC) is present in an amount of not more than 1000 ppm, and
   wherein the composition contains not more than 0.5 wt. % of water.

2. The DAFD composition of claim 1, wherein said composition comprises:
   (i) not more than 100 ppm of ACFC,
   (ii) not more than 100 ppm of AFFC,
   (iii) not more than 10 ppm of furan dicarboxylic acid (FDCA),
   (iv) not more than 100 ppm of DAFCA, and
   (v) not more than 100 ppm of ADAFC.

3. A dimethyl furan-2,5-dicarboxylate (DMFD) composition comprising solid particles of DMFD, wherein said composition comprises:
   (i) at least 98 wt. % of DMFD;
   (ii) 5-(methoxycarbonyl)furan-2-carboxylic acid (MCFC) that if present, is present in an amount of not more than 1000 ppm, and
   (iii) methyl-5-formylfuran-2-carboxylate (MFFC) that if present, is present in an amount of not more than 1000 ppm,
   wherein
   (iv) 5-(dimethoxymethyl)furan-2-carboxylic acid (DMFCA) is present in an amount of not more than 1000 ppm, and
   (v) methyl 5-(dimethoxymethyl)furan-2-carboxylate (MDMFC) is present in an amount of not more than 1000 ppm, and
   wherein the composition contains not more than 0.5 wt. % water.

4. The composition of claim 1, which contains less than 1000 ppm of furan dicarboxylic acid.

5. The composition of claim 3, which contains less than 1000 ppm of furan dicarboxylic acid.

* * * * *